(12) United States Patent
DeMeritt

(10) Patent No.: US 11,065,007 B2
(45) Date of Patent: Jul. 20, 2021

(54) ENDOVASCULAR OCCLUSIVE DEVICE AND ASSOCIATED SURGICAL METHODOLOGY

(71) Applicant: John S. DeMeritt, Saddle River, NJ (US)

(72) Inventor: John S. DeMeritt, Saddle River, NJ (US)

( * ) Notice: Subject to any disclaimer, the term of this patent is extended or adjusted under 35 U.S.C. 154(b) by 109 days.

(21) Appl. No.: 16/356,746

(22) Filed: Mar. 18, 2019

(65) Prior Publication Data
US 2019/0239894 A1 Aug. 8, 2019

Related U.S. Application Data

(63) Continuation of application No. 15/885,167, filed on Jan. 31, 2018, now Pat. No. 11,026,693.
(Continued)

(51) Int. Cl.
*A61B 17/12* (2006.01)
*A61F 2/86* (2013.01)

(52) U.S. Cl.
CPC .. *A61B 17/12113* (2013.01); *A61B 17/12031* (2013.01); *A61B 17/12045* (2013.01);
(Continued)

(58) Field of Classification Search
CPC ........ A61B 17/12022; A61B 17/12099; A61B 17/12109; A61B 17/12118; A61B 17/12131; A61B 17/12027; A61B 17/12031; A61B 17/12036; A61B 17/1204; A61B 2017/1205; A61B 17/12122;
(Continued)

(56) References Cited

U.S. PATENT DOCUMENTS 4,364,392 A * 12/1982 Strother ............. A61B 17/0057
604/103.01
4,517,979 A * 5/1985 Pecenka ........... A61B 17/12109
604/907
(Continued)

OTHER PUBLICATIONS

Mulligan, Prajapati HJS, Martin LG, Patel TH. Vascular anomalies: classification, imaging characteristics and implications for interventional radiology treatment approaches. Br J Radiol 2014;87:20130392.
(Continued)

*Primary Examiner* — Robert A Lynch
*Assistant Examiner* — Lindsey Bachman
(74) *Attorney, Agent, or Firm* — R. Neil Sudol; Henry D. Coleman

(57) ABSTRACT

A vascular plug comprises a superstructure expandable from a collapsed percutaneous insertion configuration to an expanded deployment or use configuration. The superstructure incorporates a channel or passageway and a catheter extends through the channel or passageway from a proximal side at least to a distal side of the superstructure. The central channel allows for over-the wire plug delivery and a working aperture for secondary vascular interventions under flow arrest prior to final plug release. The plug includes spring-loaded mechanical elements or clotting-enhancement structure for closing the channel or passageway upon a withdrawal or removal of the catheter from the superstructure.

31 Claims, 14 Drawing Sheets

Related U.S. Application Data

(60) Provisional application No. 62/462,576, filed on Feb. 23, 2017.

(52) U.S. Cl.
CPC .. *A61B 17/12109* (2013.01); *A61B 17/12136* (2013.01); *A61B 17/12172* (2013.01); *A61B 17/12177* (2013.01); *A61F 2/86* (2013.01); *A61B 17/1215* (2013.01); *A61B 17/12145* (2013.01); *A61B 2017/12054* (2013.01)

(58) Field of Classification Search
CPC ........ A61B 17/12127; A61B 17/12136; A61B 2017/22067; A61F 2/013; A61F 2002/011; A61F 2/01; A61F 6/20; A61F 6/22; A61F 6/225
See application file for complete search history.

(56) References Cited

U.S. PATENT DOCUMENTS

| | | | |
|---|---|---|---|
| 5,181,921 A * | 1/1993 | Makita | A61B 17/12109 604/247 |
| 5,779,672 A * | 7/1998 | Dormandy, Jr. | A61B 17/12109 604/99.04 |
| 6,022,336 A * | 2/2000 | Zadno-Azizi | A61B 17/22 604/101.05 |
| 6,165,199 A * | 12/2000 | Barbut | A61B 17/22 604/22 |
| 6,379,329 B1 * | 4/2002 | Naglreiter | A61B 17/12113 604/101.02 |
| 6,485,500 B1 * | 11/2002 | Kokish | A61M 25/104 604/101.01 |
| 6,544,276 B1 * | 4/2003 | Azizi | A61B 17/12022 604/264 |
| 6,638,293 B1 * | 10/2003 | Makower | A61B 1/3137 606/200 |
| 7,662,143 B2 * | 2/2010 | Garrison | A61M 25/1011 604/509 |
| 8,328,840 B2 * | 12/2012 | Gailloud | A61B 17/12022 606/200 |
| 8,361,104 B2 | 1/2013 | Jones et al. | |
| 8,574,258 B2 * | 11/2013 | Braun | A61B 17/12022 606/198 |
| 8,641,777 B2 | 2/2014 | Strauss et al. | |
| 8,740,961 B2 * | 6/2014 | Fulton, III | A61B 17/22 604/101.03 |
| 10,149,968 B2 * | 12/2018 | Rudakov | A61B 17/1215 |
| 2003/0040762 A1 | 2/2003 | Dorros | A61B 17/12045 606/159 |
| 2003/0187474 A1 * | 10/2003 | Keegan | A61F 2/013 606/200 |
| 2003/0229366 A1 * | 12/2003 | Reggie | A61F 2/95 606/158 |
| 2004/0143288 A1 * | 7/2004 | Searle | A61B 17/12131 606/200 |
| 2005/0014995 A1 * | 1/2005 | Amundson | A61B 1/018 600/105 |
| 2005/0107867 A1 * | 5/2005 | Taheri | A61B 17/12022 623/1.38 |
| 2005/0131453 A1 * | 6/2005 | Parodi | A61B 17/12 606/200 |
| 2006/0287668 A1 * | 12/2006 | Fawzi | A61F 2/013 606/200 |
| 2009/0018636 A1 * | 1/2009 | Gailloud | A61B 17/12022 623/1.11 |
| 2011/0319906 A1 * | 12/2011 | Rudakov | A61B 17/12109 606/127 |
| 2012/0109182 A1 * | 5/2012 | Belson | A61F 2/01 606/200 |
| 2012/0192872 A1 * | 8/2012 | Rudakov | A61B 17/12036 128/831 |
| 2012/0323270 A1 * | 12/2012 | Lee | A61B 17/12022 606/213 |
| 2013/0178891 A1 * | 7/2013 | Russell | A61F 2/013 606/200 |
| 2013/0253572 A1 | 9/2013 | Molaei et al. | A61B 17/12022 606/200 |
| 2014/0163599 A1 | 6/2014 | Wijay | A61B 17/12109 606/192 |
| 2015/0039017 A1 | 2/2015 | Cragg et al. | |
| 2015/0039020 A1 | 2/2015 | Cragg et al. | |
| 2015/0066075 A1 * | 3/2015 | Russell | A61F 2/013 606/200 |
| 2016/0030050 A1 | 2/2016 | Franano et al. | |
| 2016/0220367 A1 * | 8/2016 | Barrett | A61M 29/02 |

OTHER PUBLICATIONS

Katayoun Samadi, Gloria Maria Salazar. Role of imaging in the diagnosis of vascular malformations vascular malformations. Cardiovascular Diagnosis and Therapy publication Aug. 13, 2018.

Orlando Galego1, César Nunes1, Ricardo Morais1, Joáo Sargento-Freitas2, Francisco Sales2, Egídio Machado1. Monitoring Balloon Test Occlusion of the Internal Carotid Artery with Transcranial Doppler A Case Report and Literature Review. The Neuroradiology Journal 27: 115-119, 2014—doi:10.15274/NRJ-2014-10014.

Carotid Artery Balloon Test Occlusion. Accreditation Council on Graduate Medical Education Supplement to AJNR: 22, Sep. 2001.

Yoshimitsu OhgiyA et. al. Dynamic MRI for Distinguishing High-Flow from Low-Flow Peripheral Vascular Malformations. Musculoskeletal Imaging • Original Research. AJR:185, Nov. 2005.

Kazufumi Kikuchi et al. Balloon test occlusion of internal carotid artery: Angiographic findings predictive of results. World J Radiol Aug. 28, 2004; 6(8): 619-624.

* cited by examiner

ENDOVASCULAR OCCLUSIVE DEVICE AND ASSOCIATED SURGICAL METHODOLOGY

CROSS-REFERENCE TO RELATED APPLICATION

This application is a continuation of application Ser. No. 15/885,167 filed Jan. 31, 2018 now U.S. Pat. No. 11,026,693 and claims the benefit of U.S. Provisional Patent Application No. 62/462,576 filed Feb. 23, 2017. The entire disclosure of the prior application Ser. No. 15/885,167, is considered a part of the disclosure of the present continuation application and is hereby incorporated by reference, to be relied upon only if a portion has been inadvertently omitted from the present application as filed.

BACKGROUND OF THE INVENTION

The present disclosure generally relates to a device and methodology for occluding arterial and venous blood vessels under a variety of pathologic conditions. Many endovascular devices exist for occluding blood flow including coils, detachable balloons, and most recently expandable mechanical occlusive devices with or without coverings impervious to blood flow. Coils can be covered with fibers or coated with material such as hydrogel to enhance clot formation. Despite these features many coils are often required to occlude blood flow increasing procedure time and potentially cost. Coils can also be unreliable with regards to their geometry and vascular space filling properties after deployment. Coils can be particularly challenging to use when a precise and short segment vascular deployment location is desirable as dictated by the given vascular pathology. For example coiling over a normal adjacent branch vessel branch can occur when using coils since their deployment can be imprecise and vessel occlusion often requires multiple coils. In addition coils and or clot can easily migrate distally under high flow condition such as arteriovenous fistula in the lungs or elsewhere in the body. Blood vessels occluded by coils can reopen or recanalize as has been reported in pulmonary arteriovenous fistula. Detachable balloons can be difficult to navigate through blood vessels and can prematurely detach. Premature balloon detachment can lead to migration and occlusion of normal blood vessels resulting in complications. Balloons can deflate over time resulting in recurrence of the treated vascular pathology such as has been reported in caroticocavernous fistula. More recently detachable uncovered and membrane covered expandable mechanical occlusive devices have been developed in an attempt to occlude blood flow more rapidly and with more spatial precision; commonly referred to as vascular plugs. These include the uncovered detachable Amplatzer vascular plug which is made of a self-expanding Nitinol mesh, it is delivered through catheters or sheaths of varying size, inciting vessel thrombosis. This uncovered device may not immediately lead to thrombosis particularly in patients with clotting disorders, requiring the deployment of more than one plug The Amplatzer plug can be difficult to deliver and precisely deploy. In addition the device may not provide long-term occlusion, which has been reported in pulmonary arteriovenous fistula in particular. Covered devices such as the MVP microplug can provide immediate occlusion with good long-term occlusion in early studies. The MVP microcatheter size plug can traverse tortuous anatomy, for vessels up to 5 mm. Larger MVP covered plugs require delivery through a 5 French catheter. The device is not ideal for high flow situations with possible migration considering it's small footprint and vessel anchoring capabilities. Precise measuring or sizing relative to the target vessel is important. The relatively small length nitinol frame is best suited for straight vessel segments or horizontal deployment zones. The first over-the-wire delivery coved vascular plug or occlusive device is the EMBA Hourglass. An over-the-wire delivery platform may provide for more accurate positioning. The EMBA Hourglass is inserted via a 5 french integrated delivery catheter; it is retractable and can be repositioned after partial deployment. It has only recently been released and it remains to be seen how well the hourglass shape will occlude if placed in a tortuous or angled vascular segment. As currently configured for deployment in arteries the device consists of a downstream uncovered bell-shaped structure and an upstream covered bell-shaped structure with a constriction in the middle to thereby form an hourglass shape. The over-the-wire EMBA Hourglass plug contains a central hole or lumen for the delivery catheter and wire, which must be closed to completely stop blood flow through the plug and clot the vessel after deployment. The EMBA Hourglass achieves closure of the delivery lumen by the use of a pressure sensitive passive valve mechanism. Natural hemodynamic forces or blood pressure pinch off or close an elongated collapsible tubular segment incorporated into the plug, on the upstream side of the device, after plug deployment. It remains to be seen how well the pressure sensitive closure mechanism will work to cause complete vessel occlusion in the long-term setting or acutely under the condition of low intravascular pressure as might occur routinely in veins or occasionally in arteries. The ability of the collapsible tubular channel in the EMBA hourglass to completely occlude blood flow and clot the target blood vessel in the setting of impaired clotting or a coagulopathy is unclear.

It is desirable on many occasions to occlude a blood vessel on both the upstream and downstream sides relative to a given arterial or venous vascular pathology, i.e. to mechanically occlude a vascular segment on each side of the vascular pathology. This can be difficult and or cumbersome to achieve with current available devices. For example it can be desirable to occlude an aneurysm or abnormal ballooning of a blood vessel on both sides since the aneurysm might still fill or stay open after just upstream occlusion of the artery. Flow can reverse through collateral filling in the downstream portion of the artery relative to the aneurysm, after just upstream occlusion by a vascular plug, thereby maintaining patency of the aneurysm. Initial occlusion of the downstream portion of the vessel relative to the aneurysm can result in increased flow and pressure in the aneurysm resulting in rupture. It is generally safer under these circumstances to occlude distally only under the conditions of proximal flow and pressure control (flow arrest) to prevent possible vessel rupture; this is cumbersome and difficult by current methods. A distal and subsequently a proximal occlusive device may be delivered through an inflated balloon catheter, proximal to the vascular pathology to eliminate or reduce both flow and intravascular pressure (flow arrest). Balloon catheters are difficult to navigate and generally require large sheaths. The devices that one can use through a balloon catheter lumen are limited, necessitating extra steps and potentially multiple devices to treat the vascular pathology, both proximally and distally.

OBJECTS OF THE INVENTION

It is an object of the present invention to provide an improved vascular occlusion device and/or an associated surgical method, which addresses the afore-mentioned problems.

It is a more specific object of the present invention to provide an improved vascular occlusion device and/or an associated surgical method which enables or facilitates the deployment or installation of two tandem vascular occlusion devices or plugs in a patient's vascular system, both down stream and upstream to a given vascular pathology (vessel trapping or segmental vascular occlusion).

Another more specific objection of the present invention is to provide an improved vascular occlusion device and/or an associated surgical method wherein occlusion or interruption of blood flow is rapid and better assured than with current or conventional vascular plugs.

A further object of the present invention is to provide an improved vascular occlusion device and/or an associated minimally invasive surgical method.

These and other objects of the present invention will be apparent from the drawings and descriptions hereof. Although every object of the invention is considered to be attained by at least one embodiment of the invention, there is not necessarily any single embodiment that achieves all of the objects of the invention.

SUMMARY OF THE INVENTION

The present invention provides an endovascular occlusion device with a central working lumen to treat downstream vascular pathology through a partially deployed occlusive vascular plug resulting in a cessation of flow sufficient to implement the downstream treatment. The present method exemplarily contemplates a deployment of a secondary endovascular occlusion device downstream of the primary occlusion device. The two occlusion devices can be positioned on opposite sides of an aneurysm or other vascular pathology, isolating the pathology and preventing, or ameliorating the effects of, a more egregious bio-structural failure such as aneurysm rupture. The present invention contemplates that the primary occlusion device is removably or tentatively deployed initially, to enable repositioning of the primary device should the downstream intervention or treatment indicate. After occlusion of the vessel downstream to the vascular pathology via the working lumen of the partially deployed plug, the plug may then be fully deployed allowing for controlled occlusion on both sides of the vascular pathology.

The partial deployment of the primary plug or occlusion device results in the condition of flow arrest allowing for safer and more effective additional endovascular interventions via a central working lumen including but not limited to the deployment of a second vascular plug or coils. The partially deployed flow occlusive plug can still be recaptured and repositioned. The central working lumen or channel allows for downstream (arteries) or upstream (veins) transplug microcatheter navigation for the execution of secondary vascular interventions under flow arrest. Additional secondary vascular interventions enabled by a central working lumen under the conditions of flow arrest also include carotid artery test occlusion (in lieu of a balloon catheter) prior to carotid sacrifice with one or more plugs, deposition of liquid embolics such as N-butyl cyanoacrylate (NBCA) glue and ethylene alcohol (Onyx) in high flow vascular pathology, and venous occlusion with sclerotherapy preventing systemic reflux of the sclerosant (testicular varicocele embolization, ovarian and pelvic vein embolization in pelvic congestion syndrome embolization, and plug-assisted retrograde transvenous obliteration or PARTO).

A vascular plug in accordance with the present invention comprises a superstructure expandable from a collapsed insertion configuration to an expanded deployment or use configuration. The insertion configuration is sufficiently small to enable percutaneous introduction into a patient's vascular system. The expanded deployment or use configuration is sufficiently large to extend across a target blood vessel and engage an endothelial surface of such blood vessel. The superstructure incorporates a channel or passageway and a catheter extends through the channel or passageway from a proximal side at least to a distal side of the superstructure. The plug includes energized springloaded mechanical elements or membrane lined clot containment chamber for closing the channel or passageway upon a withdrawal or removal of the catheter from the superstructure.

BRIEF DESCRIPTION OF THE DRAWINGS

The drawings are schematic views of various embodiments of a vascular occlusion device in accordance with the invention, which may be alternatively used in carrying out a method pursuant to the invention.

FIG. 2A is a schematic perspective view of the plug or occlusion device of FIG. 1, showing the plug in a blood vessel proximate an aneurysm, the plug or occlusion device being initially partially deployed to instigate flow arrest, a central working lumen being available for distal microcatheter navigation after deployment guidewire removal.

FIG. 2B is a schematic perspective view similar to FIG. 2A, showing deployment of a navigation microcatheter and a microplug via the central working lumen of the plug or occlusion device of FIGS. 1 and 2A, with the microplug positioned downstream to the aneurysm.

FIG. 2C is a schematic perspective view similar to FIGS. 2A and 2B, showing downstream microplug deployment completed and microcatheter removed, resulting in aneurysm trapping or segmental vascular occlusion.

FIG. 2D is a schematic perspective view similar to FIGS. 2A-2C, showing the plug or occlusion device of FIGS. 1 and 2A-2C in a fully expanded permanent and membrane-covered deployment configuration, with a spring-loaded mechanical closure of a trailing plug lumen, completing segmental vessel occlusion.

FIG. 3A is a schematic perspective views of a membrane-covered version of the plug or occlusion device of FIG. 1, in a partially deployed or expanded configuration in the central portion of the left testicular vein after initial upstream deployment of a plug next to a testicular varicocele, the partially deployed covered plug acting as a backstop to prevent reflux of injected sclerosant, in accordance with the present invention. Sclerosant injection helps prevent recanalization and recurrence of the varicocele from small collateral vessels or side branches. The initially deployed upstream covered plug promotes venous occlusion and prevents reflux of sclerosant into the scrotum.

FIG. 3B is a schematic perspective view similar to FIG. 3B, depicting a later stage of a varicocele embolization with sclerotherapy, and more particularly depicting the second plug or occlusion device also in a fully deployed or expanded configuration after sclerotherapy, completing segmental venous occlusion.

DETAILED DESCRIPTION

Figure 1:
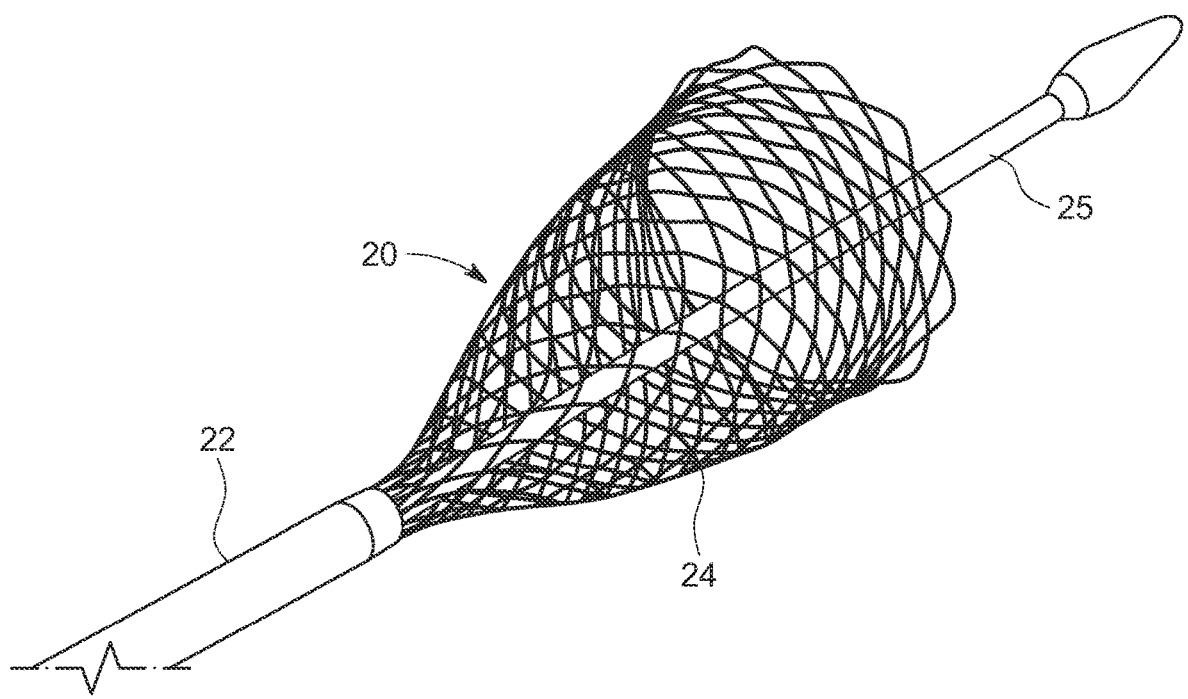
FIG. 1 is a schematic perspective view of a partially deployed leading edge of "covered plug" or occlusion device with a protruding available downstream (artery) or upstream (vein) working lumen for additional interventions (illustrated with an uncovered partially deployed self-expanding stent).
Figure 2A:
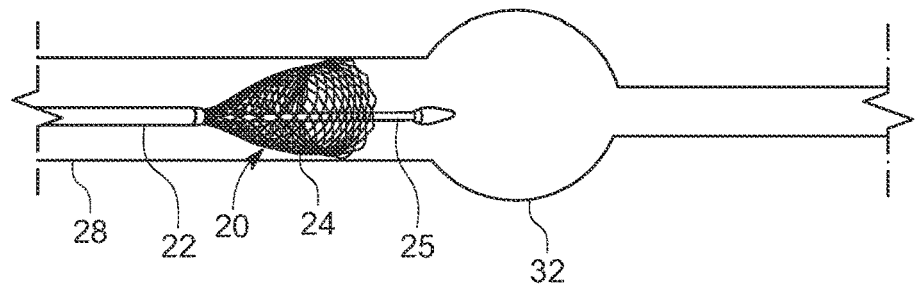
FIGS. 2A-2D pertains to segmental vascular occlusion performed in accordance with the invention described herein for treatment of an aneurysm. Note partial deployment of the over-the-wire covered plug with resultant flow arrest. The availability of a downstream central working lumen allows for distal microcatheter navigation and downstream microplug (MVP) deployment.
Figure 2B:
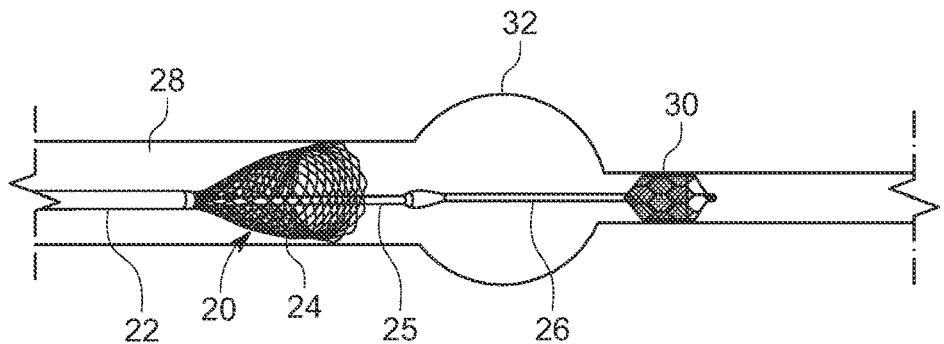
Figure 2C:
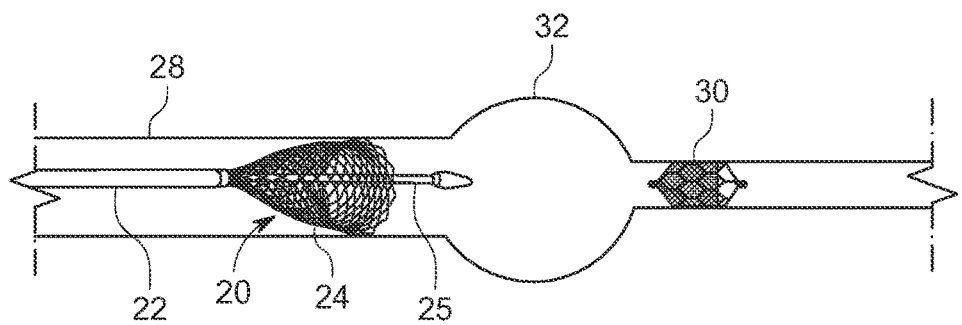
Figure 2D:
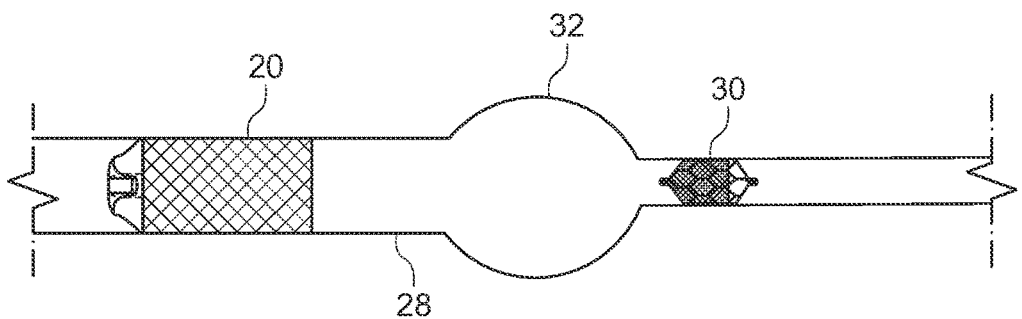

Incorporation of an intra-plug central working lumen or channel of a plug or occlusion device especially adapted for intravascular deployment is facilitated by an over-the-wire design for device delivery. A partially deployed membrane-covered occlusion device or plug 20 is depicted in FIG. 1. (An uncovered partially deployed self-expanding stent is shown for illustrative purposes). The plug 20 has a generally cylindrical fully deployed configuration (see FIG. 2D) and is partially deployed after initial withdrawal of an outer coaxial constraining deployment catheter 22 while fixing or immobilizing an inner catheter 25 in an initial stage of an occlusion operation shown in FIGS. 1 and 2A, and expanded under internal spring stresses (e.g., of a memory-shape alloy such as nitinol) to form a cone-, bell- or cup-shaped configuration 24. This expanded portion 24 of the plug 20, located on a downstream side in an arterial procedure, is similar in configuration to a covered partially deployed self-expanding vascular stent. The over-the-wire partially deployed self-expanding plug 20 is both recapturable at this point and flow occlusive. The central lumen of over-the-wire inner deployment catheter 25 is available at this initial stage for downstream arterial endeavors such a navigation with a second coaxial microcatheter 26 through an 0.038 or 0.035 inch deployment catheter lumen for example, after removal of the delivery guidewire. Partial deployment and concomitant partial expansion of the self-expanding plug 20 against a vessel wall 28 (FIGS. 2A-2C) anchors the device 20, allowing removal of the guidewire (not shown) and enabling placement of a smaller coaxial catheter 26 through the primary delivery or inner deployment catheter 25. Alternatively the device 20 may incorporate a second closeable parallel working lumen (not shown). The central working lumen may be of various sizes to allow for the insertion of different-size downstream devices. For example, in an artery, microcatheter 26 (0.38 or 0.035 inch delivery catheter working lumen) may then be used for deploying a secondary plug or occlusion device 30, exemplarily a microplug (MVP) or microcoils, as well as liquid embolics such as N-butyl cyanoacrylate (NBCA) glue and the non-adhesive copolymer ethylene alcohol (Onyx). The bell- or cup-shaped expanded portion 24 of the plug 20 enables the downstream procedure under the conditions of flow arrest, providing both downstream (arterial) and upstream (venous) mechanical or flow occlusion relative to the vascular pathology such as an aneurysm 32. After downstream arterial occlusion is achieved via the distal or secondary plug 30, the primary, proximal plug 20 may then be fully deployed, that is, the outer catheter 22 may be retracted so as to permit plug 20 to expand into its fully expanded cylindrical configuration, shown in FIG. 2D. (The term "fully expanded" is relative to the diameter of the blood vessel at the surgical implantation site, some restriction in the fully opened diameter of the plug 20 being desirable to ensure proper anchoring to the blood vessel wall 28.) After full deployment and unsheathing of the device 20 the central plug lumen is subsequently permanently closed by a spring-loaded covered mechanical element or expanding clot within an intraplug membrane lined chamber, subsequently described in detail below.

FIGS. 2A-2D depicts various sequential stages of segmental vascular occlusion facilitated by partial plug deployment with resultant flow arrest and the availability of a central working lumen for downstream (arterial) microcather navigation. As indicated above, self-expanding plug 20 is delivered through a coaxial catheter system, outer catheter 22 and inner catheter 25 being axially movable relative to each other. The outer catheter 22 withdraws over the inner catheter 25 upon which the plug 20 is mounted exposing the self-expanding plug as illustrated in FIG. 1. A pull back delivery system similar to that disclosed in U.S. Pat. Nos. 5,571,168 and 5,026,377, originally designed for self-expanding stent delivery might be utilized for deployment of the self-expanding plug 20 described herein. Incorporation of an injection side port (not shown) would allow device flushing and lubrication with saline along with injection of contrast between the coaxial catheters, exiting proximal or upstream (arteries) to the partially deployed covered plug such that flow arrest could be confirmed after partial plug deployment, prior to deployment wire removal and exposure of the central working channel. A safety release (not shown) could be incorporated into the delivery catheter to prevent premature release of the plug after partial deployment, prior to the performance of various secondary vascular interventions. A smaller or low profile version may be delivered on a 0.018-inch lumen based catheter for small vessels.

In addition to microcatheter navigation and segmental vessel occlusion the central working lumen of plug or occlusion device 20 can alternatively be used for other therapeutic purposes such as injecting sclerosants through a partially deployed plug into the upstream segment of a vein to treat a varix, preventing reflux of the agent into the systemic circulation via the partially deployed over-the-wire plug, prior to final deployment.

Figure 3A:
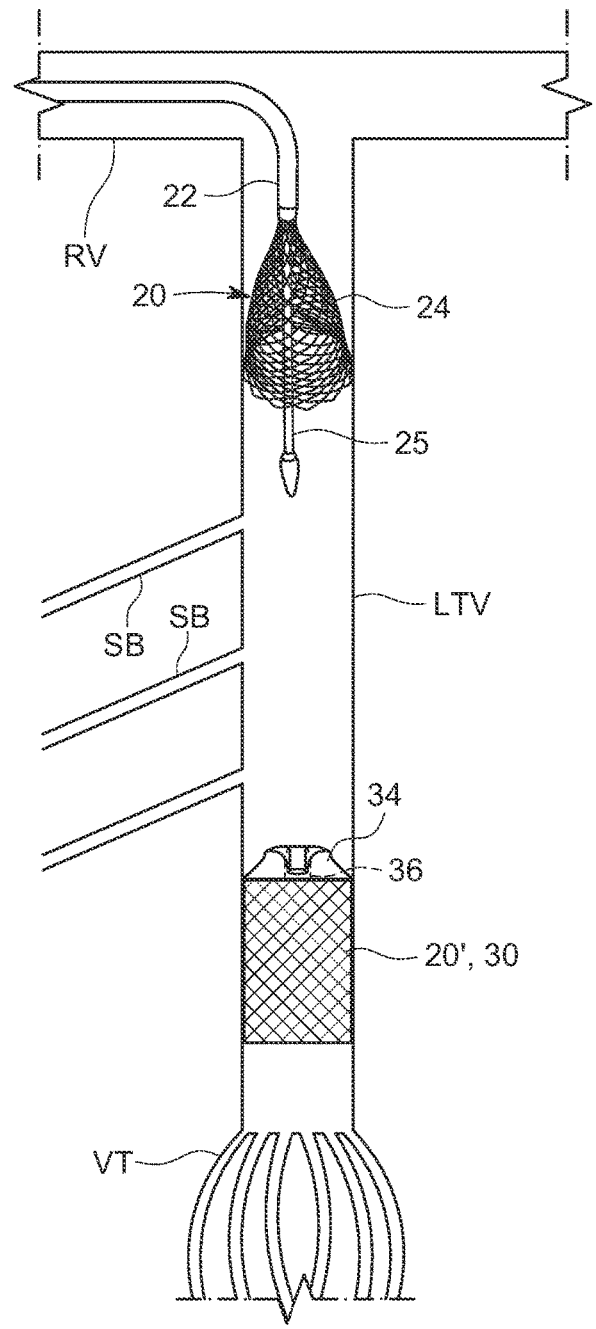
FIGS. 3A-3B pertain to segmental venous occlusion performed in accordance with the invention described herein for treatment of a testicular varicocele. The availability of a central working lumen allows for sclerosant injection without systemic reflux under the condition of flow arrest.
Figure 3B:
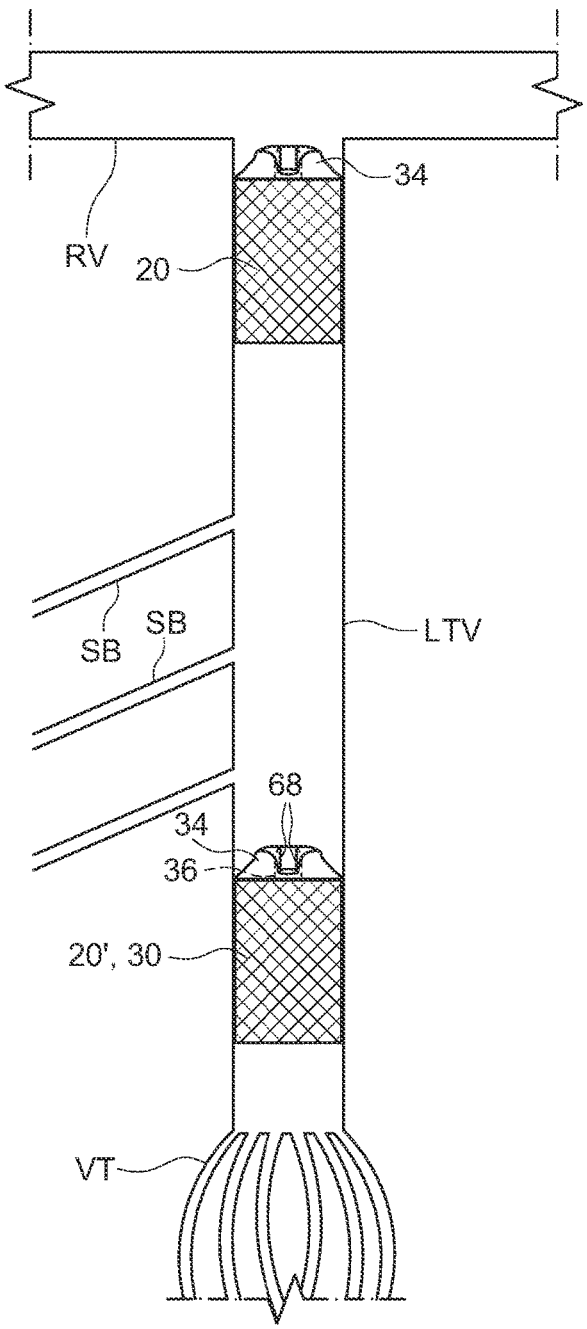

FIGS. 3A and 3B depict the use of plug 20 for the treatment of varicoceles in men. Similar principles apply to the embolization of pelvic or ovarian varices in the setting of pelvic congestion syndrome in women. FIG. 3A also shows an initially fully deployed plug as described herein in the upstream portion of the testicular vein adjacent to the testicular varicocele to promote venous occlusion and prevent egress of any subsequently injected sclerosant into the scrotum (steps of deployment not shown). Catheter 25 is subsequently inserted over a guidewire (not shown) in an upstream direction in a left renal vein RV and into the left testicular vein LTV. The outer catheter 22 constraining the plug 20 in a collapsed insertion configuration inside of it is inserted over the inner catheter 25 upon which the plug is mounted. Downstream of venous side branches SB, plug 20 is partially ejected or deployed from the outer catheter 22 (by retraction of the outer catheter 22 while simultaneously fixing or holding steady the inner catheter 25 by the operator) to form bell- or cup-shaped partial plug configuration 24 (FIG. 3A). Segmental venous sclerosis and occlusion with a trapping technique can then be performed by injecting sclerosant downstream to the initial fully deployed plug, through the partially deployed central or downstream plug, simultaneously preventing sclerosant reflux into the systemic circulation. The central or downstream plug can then be fully deployed as shown in FIG. 3B, completing segmental venous occlusion. Alternatively, as discussed above with reference to FIGS. 2A-2D, a microcatheter 26 could be inserted through catheter 25 and maneuvered to place secondary plug 30 in testicular vein LTV upstream of side branches SB and downstream of a testicular varicocele VT. To facilitate proper or effective installation of both plugs 20 and 30, plug 20 may be retracted and repositioned, as conditions warrant, prior to completion of the procedure. Upon full ejection (via withdrawal of catheter 26, leaving plug 30 in the selected position) and expansion of secondary plug 30, locking the device to the endothelial surface, a tail section 34 of plug 30 is closed via a pre-loaded active closure mechanism such as nitinol struts 36 (see discussion below). During this procedure, the partially deployed membrane-covered plug 20 acts as a backstop to prevent reflux of injected sclerosant into the systemic circulation.

As depicted in FIG. 3B, plug or occlusion device 20 is expanded to assume a fully deployed or expanded configuration after sclerotherapy, completing segmental venous occlusion.

The central working channel of plug or occlusion device 20 may be defined principally by tail section 34 and its attendant aperture or opening, allowing the inner delivery catheter upon which the plug is mounted to traverse the plug body, which ultimately contains the lumen for both the delivery wire and subsequent microcatheter navigation.

Figure 4:
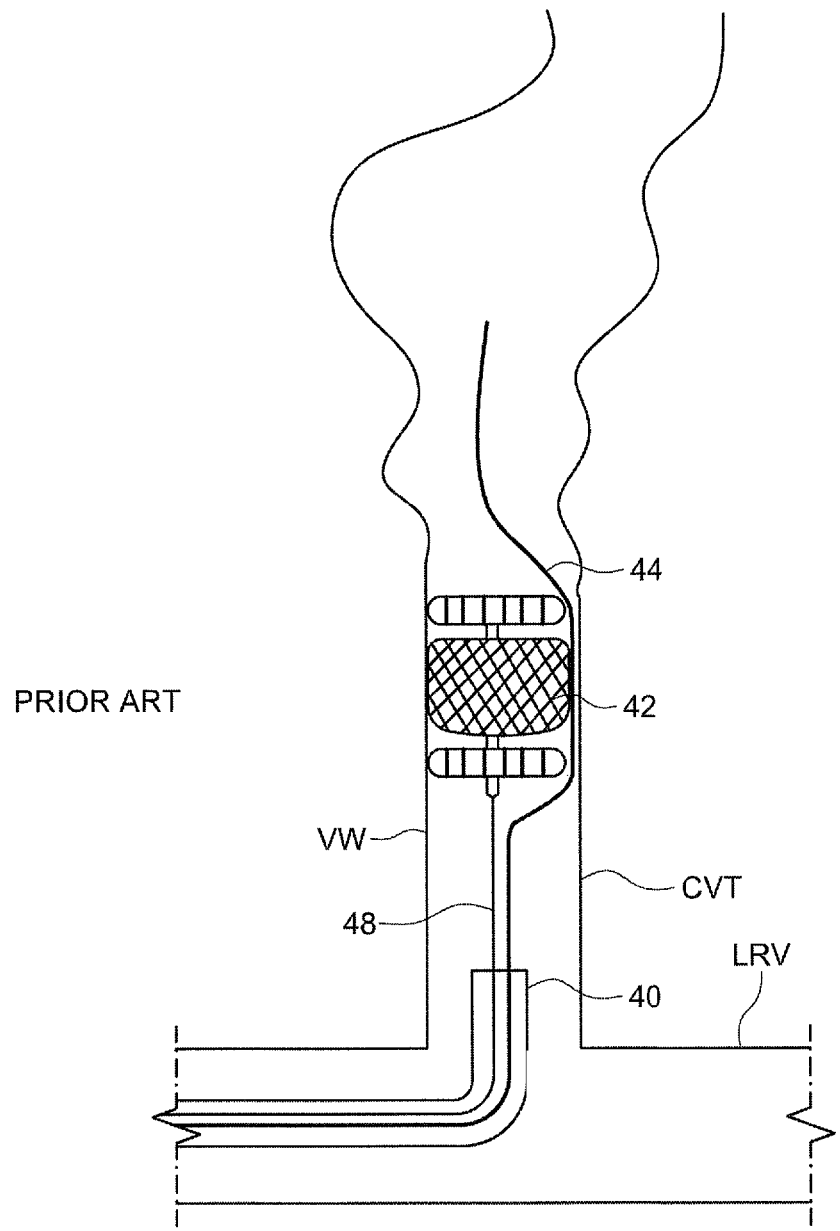
FIG. 4 is a schematic side elevational view of a conventional assembly for performing a retrograde transvenous obliteration (PARTO) procedure for treating gastric variceal bleeding, including a large caliber guiding sheath, an uncovered Amplatzer plug, and parallel 4 French catheter for gelfoam and or sclerosant injection. A deployed but still attached uncovered Amplatzer plug reduces sclerosant back flow and traps the 4 French catheter against the vessel wall for injection of gelfoam and or sclerosants. Final plug deployment typically being performed after gelfoam and or sclerosant injection and 4 french catheter removal.
Figures 5A, 5B:
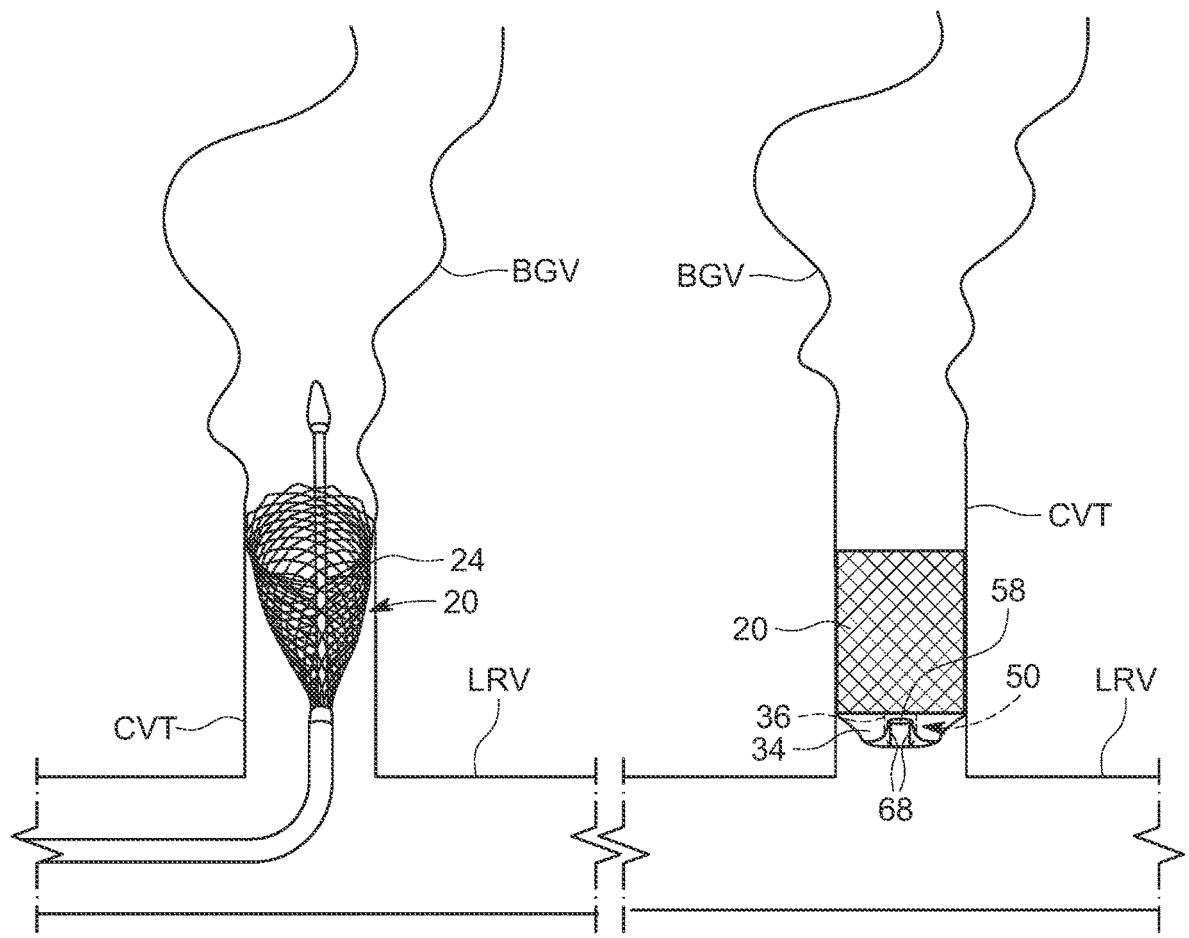
FIG. 5A is a schematic perspective view of a partially deployed vascular plug in accordance with the present invention, shown in an early step of a plug-assisted retrograde transvenous operation (PARTO) for treatment of gastric variceal bleeding, the partially deployed plug or occlusion device providing flow arrest and a central working lumen for the injection of gelfoam and/or sclerosants without reflux.
FIG. 5B is a schematic side elevational view of the plug or occlusion device of FIG. 5A, illustrates the plug or occlusion device in a fully deployed expanded configuration with closure of a trailing plug lumen by a spring-loaded mechanism completing venous occlusion.

In another procedure plug 20 may be used to segmentally occlude a venous structure or varix under the conditions of flow arrest with or without sclerosants in other parts of the body. The device is ideal for the performance of plug assisted retrograde transvenous obliteration (PARTO) of gastric varices, which can cause gastric bleeding. As depicted in FIGS. 4, 5A and 5B, a bleeding gastric varix BGV can be accessed in a retrograde fashion via a collateral venous tributary CVT which drains into the left renal vein LRV.

FIG. 4 is a schematic side elevational view of a conventional assembly for performing a retrograde transvenous obliteration (PARTO) procedure for treating gastric variceal bleeding. The instrumentation used includes a large caliber guiding sheath 40, an uncovered Amplatzer plug 42, and a parallel 4 French catheter 44 for gelfoam and or sclerosant injection. The uncovered Amplatzer plug 42 is deployed and, while still attached to an introducer wire 48 reduces sclerosant back flow and traps the 4 French catheter 44 against a vessel wall VW for injection of gelfoam and or sclerosants. Final plug deployment is typically performed after gelfoam and or sclerosant injection and removal of the 4 french catheter 44.

The uncovered Amplatzer plug 42 is the plug most commonly used for performing a plug assisted retrograde transvenous obliteration (PARTO) procedure. However, that uncovered plug 42 cannot entirely prevent systemic reflux of liquid sclerosants and may be less effective for long-term vessel occlusion relative to covered devices. PARTO is also cumbersome to perform by current methods requiring multiple pieces of equipment, as depicted in FIG. 4.

As shown in FIGS. 5A and 5B, embolization of the gastric varix BGV is also performed with various substances (often gelatin sponge and or sclerosants) upstream to an occlusive plug 20 in a vein such as a gastrorenal shunt or collateral venous tributary CVT, the application of the sponge and or sclerosants being via catheter 25. Plug 20, even in the partially expanded or deployed configurations shown in FIG. 5A, prevents reflux of the embolic material into the systemic circulation and helps occlude the gartric varix BGV. PARTO is performed utilizing a single piece of equipment, including improved prevention of sclerosant reflux into the systemic circulation via the partially deployed covered plug with flow arrest, and improved venous occlusion after final covered plug deployment relative to the uncovered Amplatzer plug. FIG. 5B depicts final plug deployment with spring-loaded or mechanical occlusion of the trailing deployment lumen, after injection of sclerosants and or gelfoam through the working channel, completing venous occlusion.

One structure for occluding the central lumen or channel of self-expanding plug 20, operative to fold over or curl the trailing or proximal end section 34 (FIGS. 2D, 3A, 3B, 5B) of the plug 20, is an energized or spring-loaded mechanical closure mechanism 50 that activates independently of biologic forces, i.e., blood pressure or flow. A spring-loaded mechanical closure of a lumen define by the trailing plug section or tail section 34 has the advantage of creating vascular occlusion independently of intravascular pressure or hemodynamic forces, in contrast to the EMBA Hourglass which is designed to close by the action of those biologic forces. Spring-loaded mechanical closure mechanism 50 is more likely to be effective under the conditions of low intravascular pressure as occurs routinely in veins and occasionally in arteries. An energized mechanical closure mechanism such as mechanism 50 may also be more effective and complete relative to a pressure sensitive valve (EMBA Hourglass) under the conditions of impaired blood clotting. Energized or active mechanical closure as disclosed herein is deemed to be more effective for the treatment of non-vascular pathology, independent of a clotting cascade such as occlusion of a ureter, bile duct, or bronchus. Energized or active mechanical closure of the delivery or working lumen of plug 20 is preferably achieved by utilizing stored potential energy in a constrained plug platform or closure such as mechanism 50. The unique shape memory and superelasticity of Nitinol alloys is satisfactory for this purpose.

Figure 6:
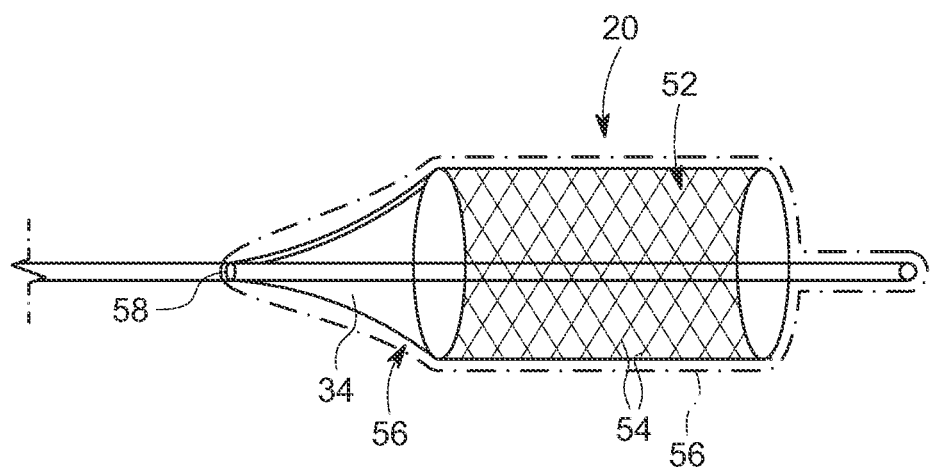
FIG. 6 is a schematic side elevational view of a partially deployed plug or occlusion device after near complete withdrawal of an outer constraining coaxial delivery catheter, in accordance with the present invention, showing the device with a trailing tail section provided with a prestressed or shape-memory strut or finger element for final lumen closure, the strut or finger element being preferably of nitinol and constrained to assume an extended generally uncoiled or expanded configuration.
Figure 7:
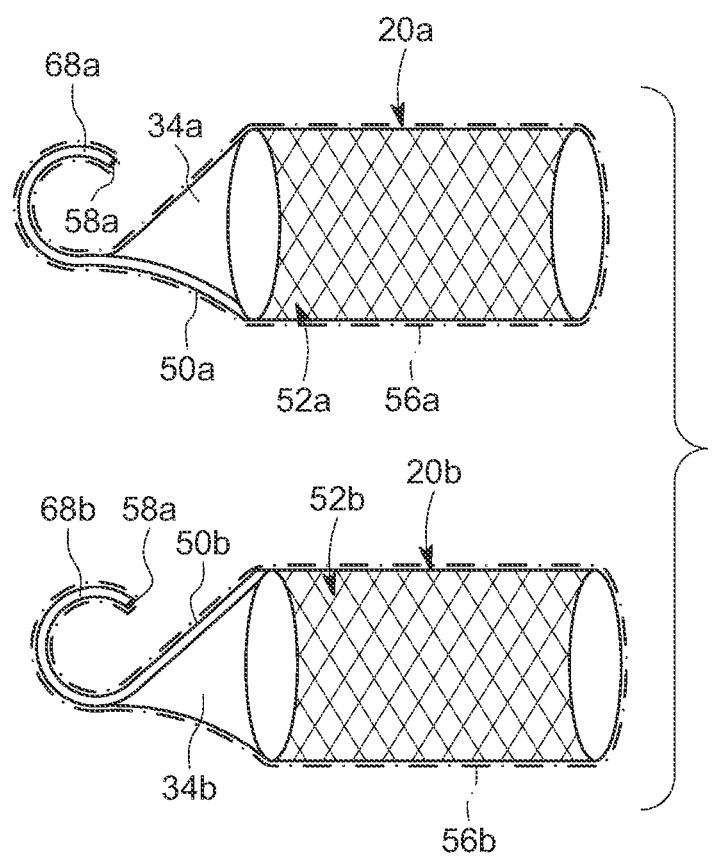
FIG. 7 is a schematic side elevational view of a pair of plugs or occlusion devices, side by side for comparison, showing the devices each in a fully expanded, fully deployed configuration with a nitinol framework in a curled shape closing or rolling up a respective trailing covered plug tail section, one plug having an superiorly positioned nitinol strut or finger and the other having a inferiorly positioned nitinol strut or finger. The radius of the curling nitinol strut might be minimized to ensure unimpeded closure of the tail section relative to the vessel diameter to which the plug body is more closely matched.

As illustrated in FIG. 6, plug or occlusion device 20 comprises a cage-like frame or superstructure 52 of crisscrossing curled or curvilinear nitinol (or other suitable material) wire strands 54 that expands from a collapsed configuration inside the outer introducer catheter or sheath 22 (FIGS. 2A-2C) into a cylindrical body member (not separately designated) covered with a membrane 56 of blood-impermeable biocompatible material such as polytetrafluorethylene. Membrane 56 includes a unitary tapered trailing segment that is tail section 34. Tail section 34 includes a proximal hole or aperture 58 that defines the central lumen of plug 20. Tail section 34 is deformable, particularly foldable or curlable, so as to close the working or deployment lumen after withdrawal or removal of the inner deployment catheter 25. The inner deployment catheter 25 serves to align or maintain the rearwardly or proximally extending tapered form of tail section 34 during a deployment procedure while the plug 20 is mounted on the inner catheter. A pull back delivery system originally designed for self-expanding stents, as disclosed in U.S. Pat. Nos. 5,571,168 and 5,026,377, is utilized for self-expanding plug delivery and deployment. The nearly completely deployed anchored plug 20, except for the tail section 34 containing the mechanical closure mechanism 50, is depicted in FIG. 6, a side elevational view. Closure mechanism 50 is connected to or an integral part of nitinol (or other alloy) frame or superstructure 52 and closes the deployment lumen (defined by tail section 34 and its hole or aperture 58) in a similar fashion to how a "party horn" curls or rolls up after it deflates. Two different embodiments 50a and 50b of closure mechanism 50 are depicted from the side of respective plugs 20a and 20b in FIG. 7. Plugs 20a, 20a include bodies, frameworks, or superstructures 52a, 52b made of crisscrossing curled or curvilinear nitinol (or other suitable material) wire strands 54a, 54b of nitinol or other shape-memory alloy that assume a fully deployed cylindrical configuration. Closure mechanisms 50a and 50b take the form of respective prestressed or shape-memory nitinol struts or finger elements that exhibit a gentle arc in the partially deployed configuration of the respective plug 20a and 20b and that automatically assume a curled closure configuration, shown in FIG. 7, that closes or rolls up a respective plug tail section 34a and 34b (tapered trailing segments that are unitary and continuous with membrane covers 56a, 56b), one plug 20a with the nitinol strut or closure mechanism 50a positioned superior to a curling side and the other plug 20b with the nitinol strut or closure mechanism 50b positioned inferior or opposite to the curling side. Struts or closure elements 50a, 50b are nitinol or other shape-memory alloy appendages of cage-frameworks 52a, 52b and extend in a proximal direction therefrom.

Figure 8:
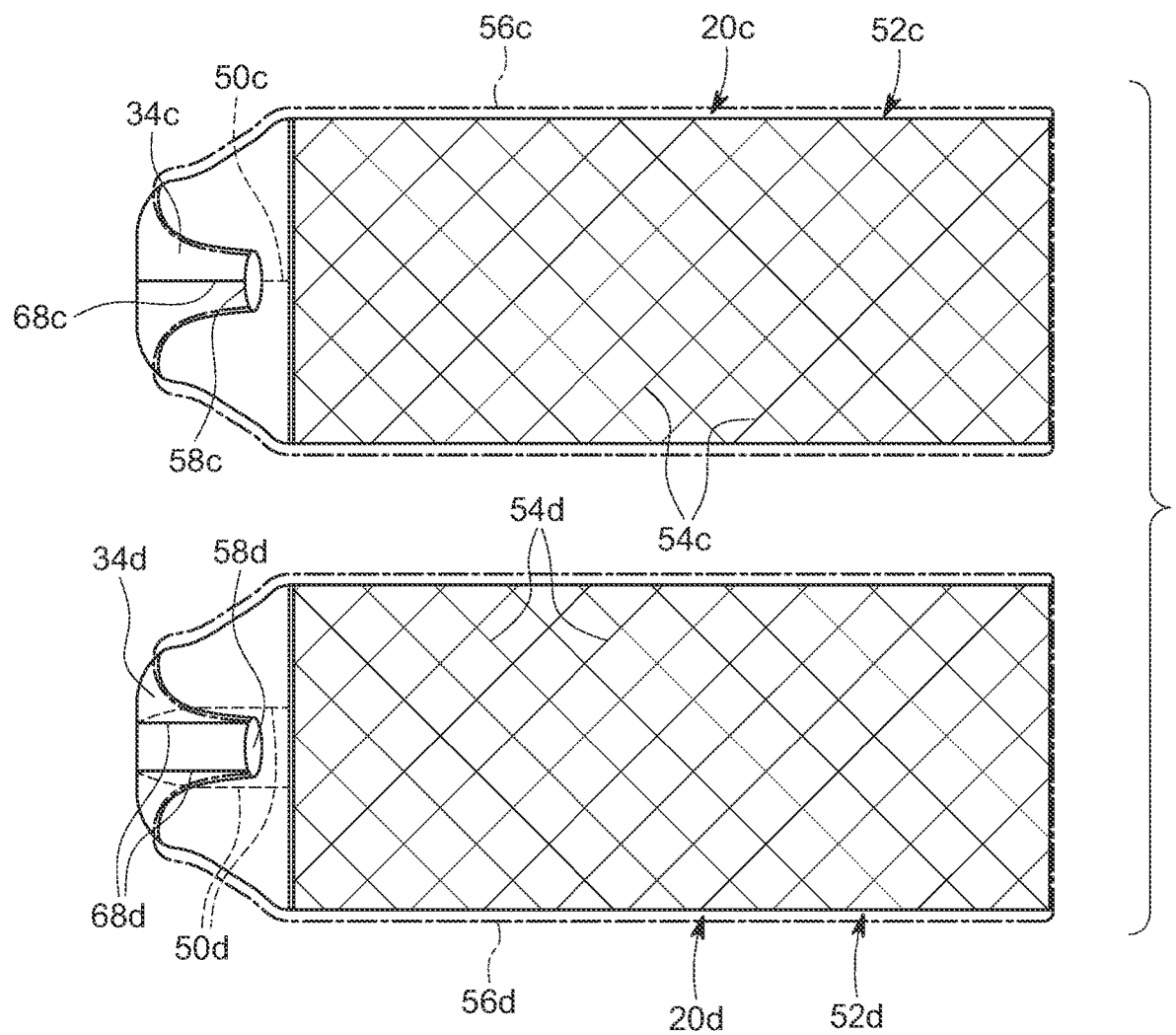
FIG. 8 is a schematic top plan view of a pair of plugs or occlusion devices, side by side for comparison, showing the devices each in a fully expanded, fully deployed configuration with a nitinol framework in a curled shape closing or rolling up a respective trailing covered plug tail section, one plug having a single nitinol strut or finger and the other having two or more nitinol struts or fingers for plug closure.

After the outer delivery or deployment catheter 22 and subsequently the inner deployment catheter 25 are both fully removed, the nitinol strut or struts 50a, 50b assume a respective predetermined coiled shape (FIG. 7), closing the tapered covered tail section 34a, 34b of the plug 20a, 20b. The radius of the curling nitinol strut might be minimized to ensure unimpeded closure of the tail section relative to the vessel diameter to which the plug body is more closely matched. Lumen-defining hole or aperture 58a, 58b and concomitantly an axis of the collapsed lumen, after the tail section 34a, 34b is folded or rolled up, no longer directly faces the direction of blood flow. The form of the folded or rolled-closed trailing or tail section 34, 34a, 34b is like the form of tail sections 34c and 34d of plugs 20c, 20d shown in top view in FIG. 8, wherein closure mechanism 50 takes the form of a single strut or finger element 50c or a plurality of struts or finger elements 50d, respectively. While FIG. 8 shows the struts or finger elements 50c, 50d disposed on a side opposite the curled side as in plug 20a (FIG. 7), the struts or finger elements may alternatively be disposed on the same side as the curl as in plug 20b. Pursuant to the disclosure above, struts or finger elements 50c, 50d are nitinol or other shape-memory alloy appendages of cage-frameworks or superstructures 52c, 52d and extend in a proximal direction therefrom. Tail sections 34c, 34d are unitary tapered trailing segments of plug covers 56c, 56d which are membranes of polytetrafluoroethylene, GORTEX™, or other bio-compatible material (see below). Plug covers or membranes 56c, 56d envelop cage-like body members or superstructures 52c, 52d, which comprise interwoven strands, wires or filaments 54c, 54d of nitinol or other shape memory material that induce automatic expansion of plugs 20c, 20d upon a retraction of outer delivery or deployment catheter 22 (see FIGS. 1, 2A-2C, 3A), in the proximal direction. Tail sections 34c, 34d have free ends, opposite the respective cage or body member 52c, 52d, provided with lumen-defining holes or apertures 58c, 58d.

Figure 9:
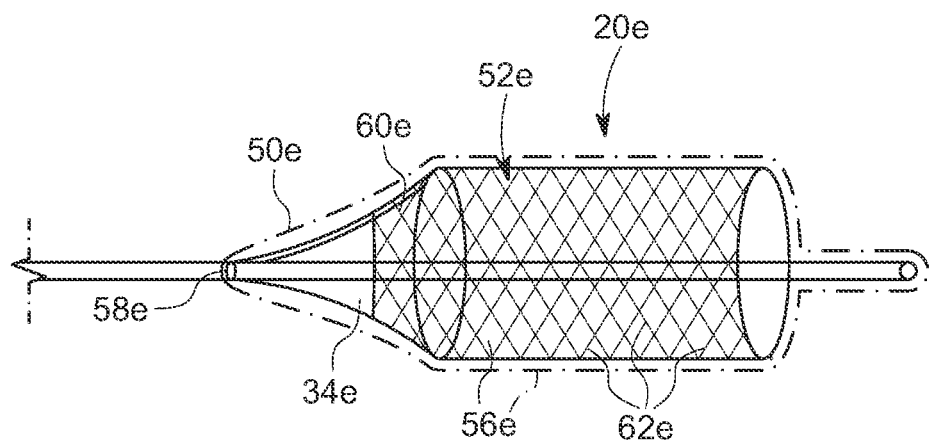
FIGS. 9 and 10A are schematic side elevational views of a plug or occlusion device in accordance with the present invention, FIG. 9 showing an alternative or modified tapering plug body in a partially deployed configuration wherein a shortened trailing tail section incorporates a nitinol framework or cage structure extending from the main body of the plug, thereby reducing the size and profile of the terminal curled tail segment, and FIG. 10A showing a fully deployed configuration of the plug or occlusion device wherein a nitinol strut has caused the tail section to assume a curled configuration effectuating lumen closure, the nitinol strut being located on the same side of the tail section as the curl. A smaller lower profile trailing tail section might ensure unimpeded curing and closure of the plug relative to the outer diameter of the target blood vessel to which the leading plug body is more closely matched.
Figure 10A:
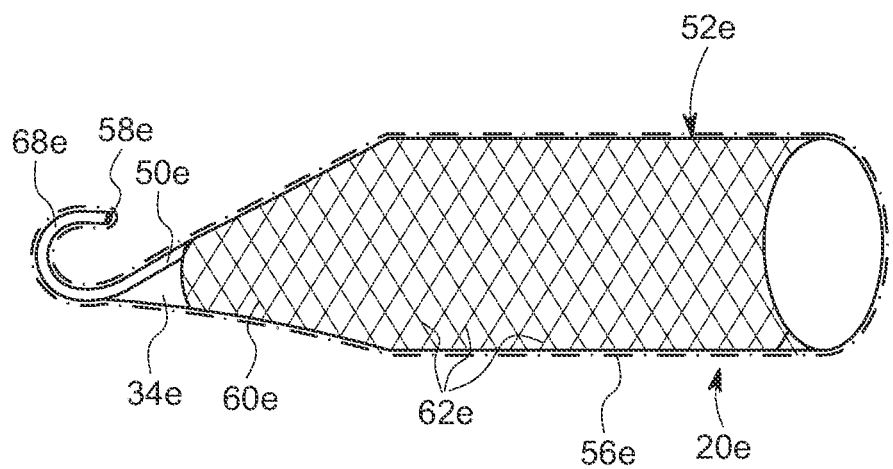

In another plug 20e, a cage or body frame superstructure 52e includes a tapered proximal extension 60e with a shorter membrane tail section 34e having a lower profile, shown partially deployed in FIG. 9, and fully deployed in FIG. 10A. Smaller lower profile trailing or tail section 34e, facilitated by a tapering plug body, at 60e, is intended to ensure unimpeded curing and closure of the plug tail relative to the outer diameter of the target blood vessel to which the leading plug body is more closely matched. A lumen-closing strut or finger 50e is connected to and extends proximally of cage or body frame superstructure 52e and is provided on the curling side. As in all other embodiments disclosed herein, cage or body frame superstructure 52e is an expandable network of crisscrossing and mutually lockable wires or strands 62e made of nitinol or other shape-memory alloy and covered with a fluid-impermeable membrane 56e. Cage or body frame superstructure 52e may be collapsed from a partially opened configuration having a conical, cup-shaped or bell-shaped expanded distal end portion as indicated at 24 in FIGS. 1 and 2A-2C.

Tail section 34e is a unitary tapered trailing segment of plug cover or membrane 56e, which is made of polytetrafluoroethylene, GORTEX™, or other bio-compatible material (see below). Tail section 34e has a free end, opposite cage or body member 52e, which is provided with a lumen-defining hole or aperture 58e.

Figure 10B:
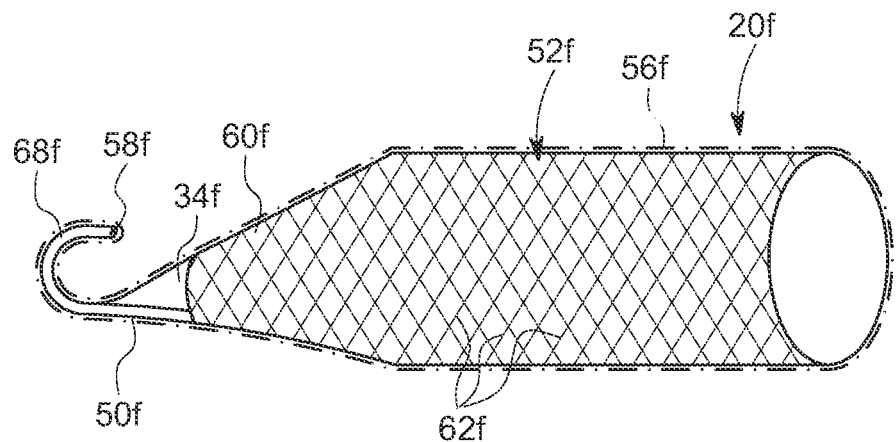
FIG. 10B is a schematic side elevational view of another plug or occlusion device pursuant to the present invention, similar to that of FIGS. 9 and 10A, showing the device with a prestressed or shape-memory nitinol strut or finger element in a curled closure configuration closing or rolling up a respective trailing covered plug tail section, with the nitinol strut positioned inferior or opposite to the curling side, the plugs of FIGS. 9, 10A, 10B having a tapered plug framework integral with a framework of a cylindrical plug body and with a shorter and lower profile tail closure section.

FIG. 10B illustrates a plug 20f that is a variant or modification of plug 20e of FIGS. 9 and 10A. Plug 20f has a cage or body frame or superstructure 52f including a tapered proximal extension 60f with a shorter membrane tail section 34f and lower profile, shown fully deployed. A smaller lower profile tail section, facilitated by a tapering plug body, is intended to ensure unimpeded curing and closure of the plug tail relative to the outer diameter of the target blood vessel to which the leading plug body is more closely matched. A lumen-closing strut or finger 50f is connected to and extends proximally of cage or body frame 52f and is provided opposite the curling side. Cage or body frame 52f is an expandable network of crisscrossing and mutually lockable wires or strands 62f made of nitinol or other shape-memory alloy and covered with a fluid-impermeable membrane 56f. When warranted during an intra-lumen procedure in order to enable plug repositioning, cage or body frame 52f may be collapsed from a partially opened configuration having a conical, cup-shaped or bell-shaped expanded distal end portion as indicated at 24 in FIGS. 1 and 2A-2C. This option is inherent in all of the occlusion devices or plugs 20, 20a-20i disclosed herein. Tail section 34f terminates, on a proximal side, opposite body member 52f, in a hole or aperture 58f that defines a lumen accommodating inner deployment catheter 25 (FIGS. 1, 2A-2C, 3A).

Figure 11:
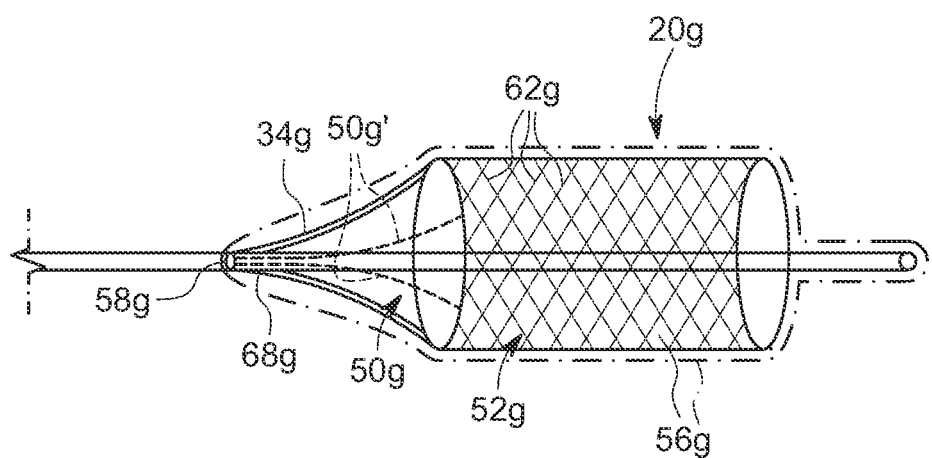
FIG. 11 is a schematic side elevational view of a partially deployed covered plug with a trailing tail section in an extended or pre-closure configuration, the tail section containing four nitinol pincer struts for lumen closure, an alternative means for energized or spring-load mechanical closure of the delivery lumen and working channel.
Figure 12A:
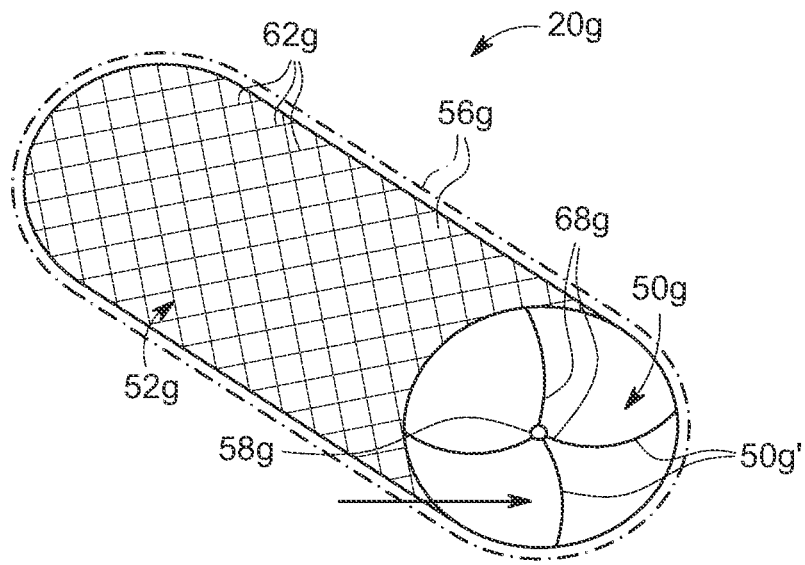
FIGS. 12A and 12B are a schematic isometric end view and a schematic side elevational view of another membrane-covered plug or occlusion device in accordance with the present invention, showing the plug in a fully deployed configuration with a pincer nitinol framework having four nitinol struts closing a circular deployment lumen of a trailing covered plug tail section. Excess or unsupported membrane extending beyond the terminal ends of the nitinol pincers may become crimped or flattened and form an ancillary closure secondary to constriction or folding over of the terminal material by the struts or pincers in the fully deployed state (not shown).
Figure 12B:
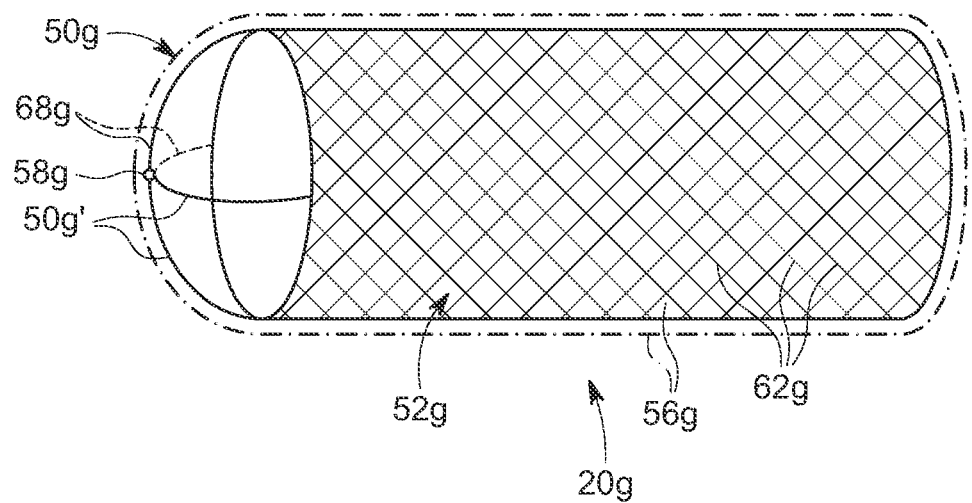

An alternative energized or active mechanical closure mechanism is incorporated into a plug or occlusion device 20g to close a deployment lumen, the closure mechanism taking the form of a nitinol pincer mechanism 50g with four separate struts 50g' closing a round deployment lumen 58g as depicted partially deployed in FIG. 11 and fully deployed in FIGS. 12A and 12B. Lumen-closing pincer-type mechanical closure struts 50g are angularly equispaced and extend proximally of a cage or body frame 52g. Cage or body frame 52g is an expandable network or superstructure of crisscrossing and mutually lockable wires or strands 62g made of nitinol or other shape-memory alloy and covered with a fluid-impermeable membrane 56g. Cage or body frame 52g may be collapsed from a partially opened configuration having a conical, cup-shaped or bell-shaped expanded distal end portion as indicated at 24 in FIGS. 1 and 2A-2C.

In all the embodiments disclosed herein, the mechanical lumen-closing struts 36 (FIGS. 3A, 3B, 5B and 6) and 50a-50f and 50g' are connected, at least at proximal ends 68, 68a-68g of the struts, to the respective tail sections 34, 34a-34g of the respective plugs 20, 20a-20g proximate the lumen-defining holes or apertures 58, 58a-58g of the tail sections. In contrast to the action of mechanical closure mechanisms or struts 50a-50f, struts 50g serve to crimp the lumen-defining hole or aperture 58g in tail section 34g upon withdrawal of inner delivery or deployment catheter 25. Closure mechanisms or struts 36, 50a-50f fold or curl the respective tail sections 34, 34a-34f. The crimping, infolding, and collapsing of unsupported covering membrane extending beyond the ends of the pincer struts may provide a secondary closure effect supplementing that of the closure mechanisms or struts 50g.

Figure 13A:
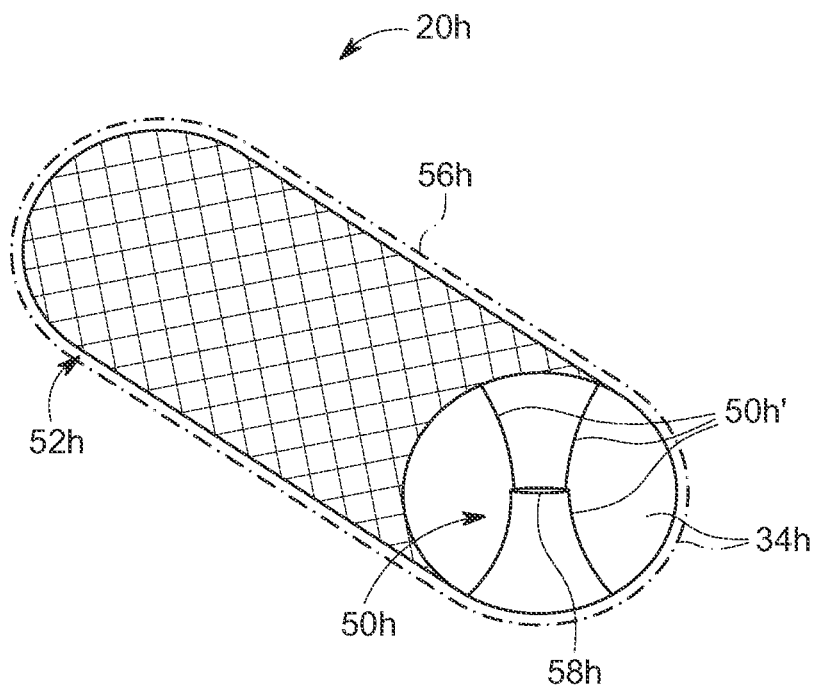
FIGS. 13A and 13B are a schematic isometric end view and a schematic side elevational view of a further membrane-covered plug or occlusion device in accordance with the present invention, showing the plug in a fully deployed configuration with a pincer nitinol framework having four nitinol struts closing a "fish-mouth" deployment lumen of a trailing covered plug tail section.
Figure 13B:
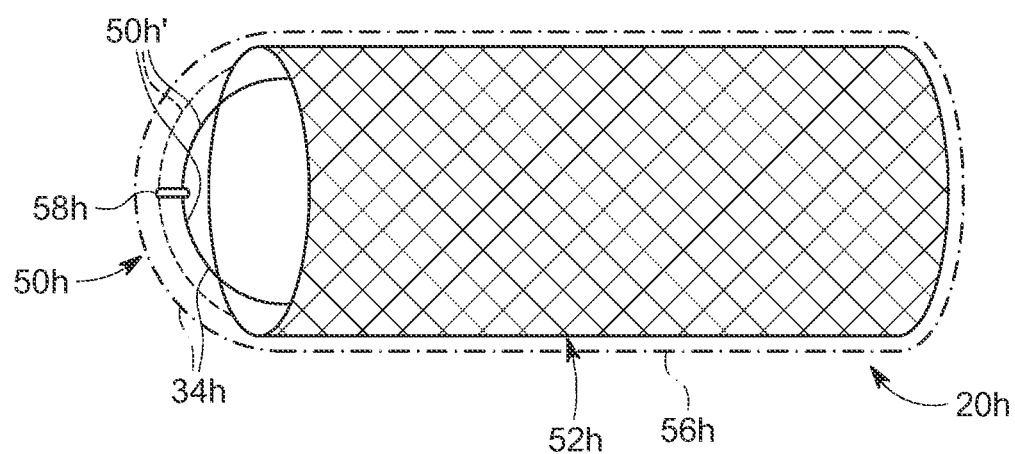

A similar pincer mechanism 50h with four struts or fingers 50h' is depicted as a component of a plug or occlusion device 20h in FIGS. 13A and 13B. Struts 50h' are connected at their distal ends to an expandable nitinol or shape-memory-alloy cage or frame 52h and at their proximal ends to a tail section 34h with a "fish mouth" or slit-like opening or aperture 58h defining a deployment lumen, as opposed to a round lumen 58g as shown in FIGS. 12A and 12B. A PTFE membrane 56h covers the cage superstructure or frame 52h and is preferably integral with tail section 34h.

Figure 14A:
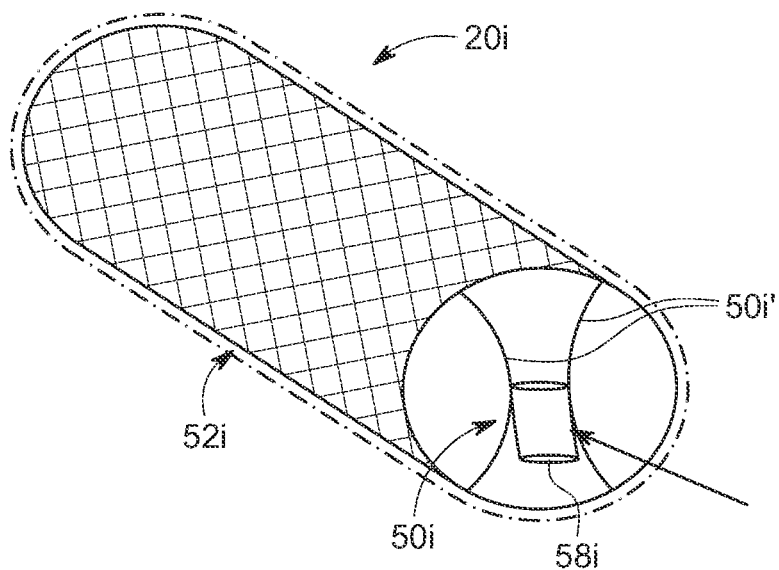
FIGS. 14A and 14B are a schematic isometric end view and a schematic side elevational view of a further membrane-covered plug or occlusion device in accordance with the present invention, showing the plug in a fully deployed configuration with a pincer nitinol framework having four nitinol struts closing a "fish-mouth" deployment lumen, and including an unsupported membrane covered terminal section of a plug tail.
Figure 14B:
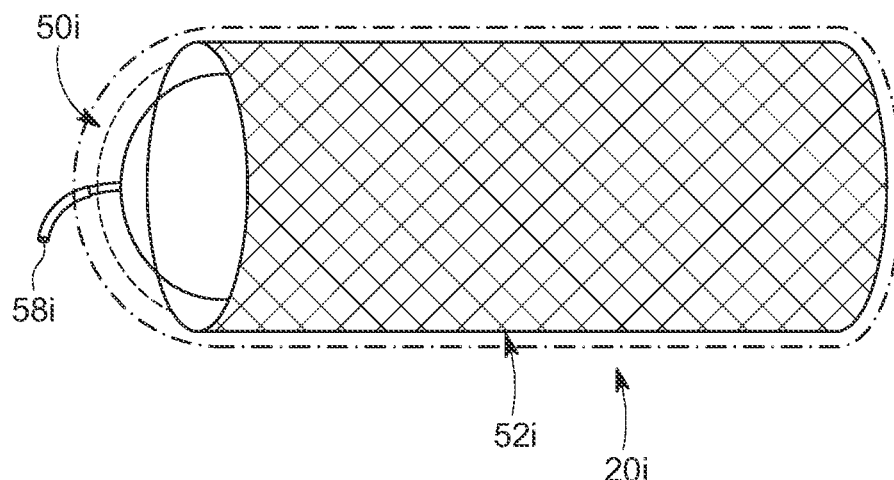

FIGS. 14A and 14B depict a plug or occlusion device 20i with a cage frame or superstructure 52i, a similar pincer closure mechanism 50i and a similar slit-like opening or aperture 58i defining a deployment lumen as in FIGS. 13A and 13B with the addition of a short unsupported tail segment 70, for ensuring lumen closure.

In summary, potential energy in the constrained plug platform or cage frame 52 (FIGS. 3A, 3B, 5B and 6) and 52a-52i and in the lumen-closing mechanism 36 (FIGS. 3A, 3B, 5B and 6) and 50a-50i is responsible for both anchoring the respective plug 20 and 20a-20i against a vessel wall and energized mechanical closure of the deployment lumen. Plug anchoring (leading or distal end) occurs prior to engagement or initiation of the resistive forces on the inner deployment catheter 25 inherent in the spring-loaded mechanical luminal closure mechanism located in the trailing or proximal end. Resistive forces exerted on the inner deployment catheter 25 (after removal or withdrawal of the outer catheter) by the mechanical lumen closure mechanism 36, 50a-50i must be less than the radial anchoring force of the deployed plug 20, 20a-20i against the vessel wall to enable plug deployment and prevent device migration. The energized or spring-loaded mechanical luminal closure mechanisms 36, 50a-50i described herein may take additional forms varying the number, positions, and locations of the various nitinol (or other metals or alloys) closure struts or coils (36, 50a-50f, 50g', 50h', 50i). Various energized or active mechanical hinge or lever arm closure mechanisms may be utilized for a similar purpose and method. The closure struts 36, 50a-50f, 50g', 50h', 50i may be laser-cut from nitinol tubing as part of the main stent body 52, 52a-52i. Alternatively lap welds may be utilized to attach the closure struts 36, 50a-50f, 50g', 50h', 50i (nitinol) or mechanical closure mechanism 36, 50a-50i to the main part of the plug body or frame 52, 52a-52i. Similarly the main plug frame 52, 52a-52i, tapered or not, may be constructed out of various metals or metal alloys including but not limited to nitinol. The plug membrane covering 56, 56a-56h, which is included in every plug or occlusion device 20, 20a-20i, can be made of, but is not limited to, PTFE, Teco Thane, nylon, PET, Carbothane (Bionate), fluoropolymer, SIBS, and PGLA.

Figure 15A:
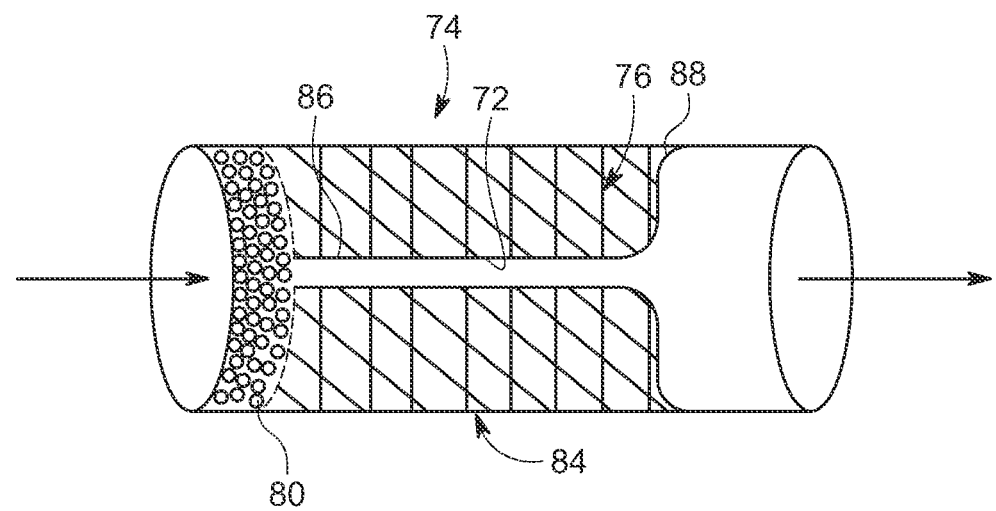
FIGS. 15A and 15B are schematic side elevational views of another plug or occlusion device in accordance with the present invention, having a central deployment channel and final downstream coverings that are impervious to flow and further having a plurality of porous membranes from upstream end (left) towards downstream end with sequentially smaller pores to create stasis and promote clot formation, expanding clot being trapped by the membranes and secondarily closing the central lumen.
Figure 15B:
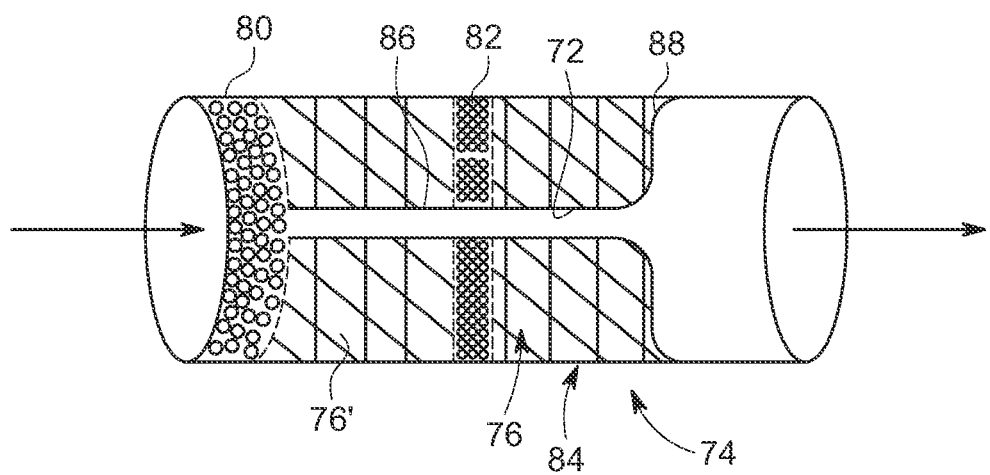
Figure 16:
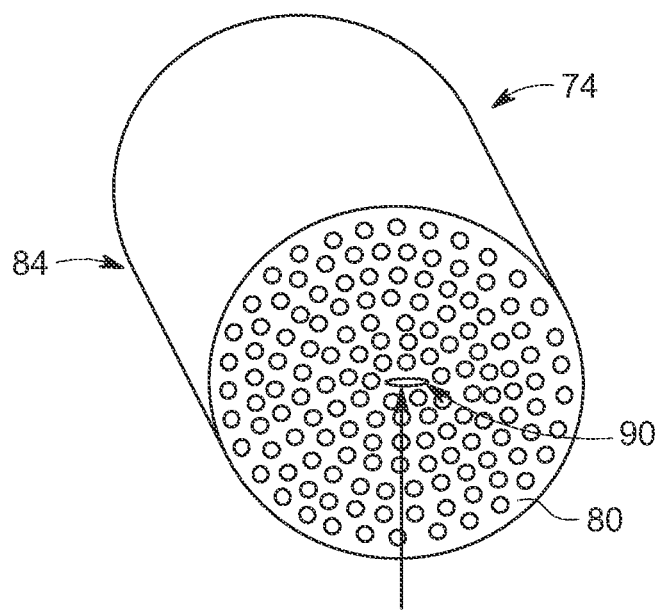
FIG. 16 is a schematic isometric end view of a porous membrane self-expanding plug in accordance with the present invention, having a slit-like deployment lumen and oriented in the direction of blood flow.

FIGS. 15A and 15B depict another mechanism for closing a central lumen 72 of an over-the-wire self-expanding plug 74 is based on promoting and trapping expanding clot within one or more intra-plug compartments or chambers 76, thereby secondarily mechanically closing or pinching off a centrally located blood flow impervious tubular membrane lined channel 78. One or more porous membranes 80, 82 (dotted surfaces) are placed in series within a cylindrical cage or framework 84. As the blood enters intra-plug compartment(s) or chamber(s) 76 surrounding an axial tube 86 defining central deployment lumen or channel 72, which tube is impervious to blood flow (solid gray); a terminal membrane 88 also impervious to blood flow prevents flowing blood from leaving the intra-plug chamber(s) or compartment(s) 76. The outer portions of the plug cage or framework 84 may be fully covered, partially covered, or uncovered. The intra-plug compartment(s) 76 may at least be partially created by the surrounding blood vessel wall. Various porous and non-porous membranes or coverings 80, 82 are suspended from the self-expanding stent-like cage or framework superstructure 84. Flowing blood enters an initial intra-plug chamber or compartment 76' via relatively porous or large-pore membrane 80 covering the upstream end of the plug 74 having a large surface area relative to the deployment lumen 72 and associated tube 86, (see FIG. 16). After blood enters the initial intra-stent compartment 76' one or more additional membranes 82 placed in series, and having successively smaller pores, foster stasis and clot formation. Expanding clot trapped by the porous membranes 80, 82 and the terminal downstream impervious membrane or cover 88 secondarily closes or pinches off the axial tube 86 and concomitantly central deployment lumen 72, the walls of which are impervious to blood flow. The porous membranes 80, 82 allow fresh clotting factors to enter the intra-stent compartment(s) 76, 76'. Intra-stent surfaces such as the outer surface of the central tube 86 may be coated with thrombogenic material to foster clot formation. Normal red blood cells measure 6-8 microns, which define the lower limits of the pores of membranes 80, 82 contained within the stent plug 74. The central deployment lumen 72 and upstream orifice 90 (FIG. 16) may be modified in various ways to minimize blood flow after removal of the deployment catheter, thereby promoting its closure. A slit-like form of orifice 90 and a compliant collapsible oval configuration of the central deployment lumen 72 (i.e., tube 86) aids in secondary mechanical closure by the expanding intra-plug blood clot. The design allows for a central working channel after partial plug deployment similar in principle and design to the energized or active mechanical closure mechanisms 50a-50i of FIGS. 1-14B.

Any of the occlusion devices described herein can include one or more radiopaque markers that permit fluoroscopic visualization of the plug 20a-20i and 74 and the delivery system during various stages of deployment, partial deployment, retraction, and after final plug release.

Described herein are two over-the-wire covered vascular plugs (one including plugs 20a-20i, the other plug 74) for occluding blood vessels. The plugs 20a-20i and 74 both incorporate a central working channel (openings 58a-58i and lumen 72) to enable additional vascular interventions after initial partial plug deployment. These interventions include but are not limited to segmental vascular occlusion or vessel trapping in both arteries and veins respectively under flow arrest and injecting sclerosants or other embolic material in veins without allowing reflux into the systemic circulation. The plug can then be fully deployed after completion of these additional secondary interventions. The design includes closure of a central plug working lumen or channel incorporated in an over-the-wire plug by two different means. The first employs an energized or spring-loaded mechanical method, after partial plug deployment and anchoring, to close the trailing plug segment and central channel. The energized mechanical closure is advantageous in the setting of impaired clotting and low intravascular pressure over current means and methods. The second over-the-wire design exploits intra-plug expanding clot to mechanically close the central plug channel. A series of one or more blood-semipermeable membranes in combination with blood-impermeable membranes create stasis within intra-stent chambers or compartments, trapping the expanding clot and secondarily compressing or pinching closed the central tubular channel.

The provision of a closeable channel or passageway in a vascular plug device enables the occlusion of a blood vessel and the performance of a procedure on a distal side of the partially deployed plug via a catheter traversing the channel or passageway. The procedure may entail the deployment of a second plug, for instance, on an opposite side of an aneurysm from the first plug. The second plug may be inserted in a collapsed configuration through the catheter or may be inserted with the first plug, both initially in a collapsed configuration but the second plug distal of the first plug. At a target surgical site in a blood vessel, the first plug is deployed to occlude the blood flow. Thereafter the second plug is expanded and fully deployed. Then the second plug is detached from the distal end of the catheter, the catheter is withdrawn through the channel or passageway in the first plug, and the channel or passageway is collapsed exemplarily via spring loaded mechanical elements or clotting-enhancement structure as described herein above.

Inner deployment catheter 25 may be provided with a low-friction layer on an outer surface so that plug 20, 20*a*-20*i* is not entrained by the catheter and does not migrate during final removal of the inner catheter. More particularly, the low-friction layer facilitates extraction of catheter 25 without sticking to the respective tail section 34, 34*a*-34*g* and thereby causing undesirable plug migration.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A medical method comprising:
   providing a flow occlusive medical device having a superstructure;
   inserting, into a target blood vessel of a patient in a direction of blood flow, said medical device with said superstructure in a collapsed configuration;
   thereafter expanding said superstructure of said flow occlusive medical device from the collapsed configuration to an at least partially expanded deployment or use configuration inside the target blood vessel of the patient so that the at least partially expanded superstructure extends across the target blood vessel and engages an endothelial surface of such blood vessel upstream of a vascular pathology to cause flow cessation or arrest through said target blood vessel;
   via a catheter extending through a channel or passageway in said superstructure, conducting an occlusive surgical intervention to insert or deploy a first flow-occlusion implant on a distal side of the at least partially expanded deployment or use configuration of said superstructure and on a downstream side of said vascular pathology;
   after completion of said occlusive surgical intervention, removing said catheter from said superstructure;
   permanently closing said channel or passageway after withdrawal or removal of said catheter from said superstructure; and
   after the permanent closing of said channel or passageway, leaving said flow occlusive medical device implanted in said target blood vessel to form a second flow-occlusion implant therein spaced from said first flow-occlusion implant and to create therewith a segmental vessel occlusion of said vascular pathology.

2. The method defined in claim 1 wherein the permanent closing of said channel or passageway includes automatically or actively operating a mechanical closure independently of blood pressure.

3. The method defined in claim 2 wherein said mechanical closure incorporates a shape-memory metal or alloy element for spring-loaded closure.

4. The method defined in claim 3 wherein said mechanical closure is disposed at a trailing or proximal end of said occlusive medical device and includes a plurality of mechanical closure elements angularly equispaced and extending on a side of said superstructure opposite said first flow-occlusion implant, said mechanical closure having a pre-closure configuration tapering down in a proximal direction away from said superstructure, the permanent closing of said channel or passageway including moving said mechanical closure elements.

5. The method defined in claim 3 wherein said mechanical closure includes a trailing or proximal end section of said occlusive medical device, the permanent closing of said channel or passageway including curling said trailing or proximal end section.

6. The method defined in claim 4 wherein said occlusive medical device has excess or unsupported membrane material that extends beyond terminal ends of said mechanical closure elements and that is crimpable or flattenable to form an ancillary closure secondary to constriction or folding over of the terminal material by said mechanical closure elements in a fully deployed state of said occlusive medical device.

7. The method defined in claim 1 wherein the conducting of said occlusive surgical intervention includes deploying a flow-occlusion auxiliary device as said first flow-occlusion implant in said target vessel on the downstream side of said vascular pathology opposite the expanded superstructure of said flow occlusive medical device, the deployed flow-occlusion auxiliary device as said first flow-occlusion implant and the implanted flow occlusive medical device as said second flow-occlusion implant together isolating said vascular pathology from a vascular system of the patient and resulting in said segmental vessel occlusion.

8. The method defined in claim 1 wherein said at least partially expanded deployment or use configuration includes an expanded configuration of a distal portion of said superstructure of said flow occlusive medical device adapted to cause flow cessation or arrest through said target blood vessel and a pre-expansion collapsed state of a proximal end portion of said superstructure.

9. The method defined in claim 1 wherein the conducting of said occlusive surgical intervention includes deploying or depositing flow-occlusion embolics in said target blood vessel.

10. The method defined in claim 9 wherein the flow-occlusion embolics are taken from the group consisting of N-Butyl cyanoacrylate, ethylene alcohol, gelfoam, and sclerosants.

11. The method defined in claim 1 wherein said vascular pathology is taken from the group consisting of a high-flow vascular pathology, an aneurysm, a varicocele, and varices.

12. The method defined in claim 1 wherein the conducting of said occlusive surgical intervention includes deploying flow-occlusion embolics taken from the group consisting of mechanical devices, gelfoam, and liquid materials.

13. The method defined in claim 12 wherein the flow-occlusion embolics are taken from the group of liquid materials consisting of N-Butyl cyanoacrylate, ethylene alcohol, and sclerosants.

14. The method defined in claim 12 wherein the flow-occlusion embolics are taken from the group of mechanical devices consisting of coils and plugs.

15. The method defined in claim 1 wherein said first flow-occlusion implant is a flow-occlusive device and wherein the conducting of said occlusive surgical intervention includes deploying said flow-occlusive auxiliary device in said target blood vessel.

16. A medical method comprising:
providing a first flow occlusive medical device having a superstructure;
inserting, into a vascular system of a patient, said medical device with said superstructure in a collapsed configuration;
thereafter expanding said superstructure from the collapsed configuration to an expanded deployment or use configuration inside a target blood vessel in the vascular system of the patient so that the expanded superstructure extends across the target blood vessel and engages an endothelial surface of such blood vessel at a first location on one side of a vascular pathology;
via a catheter extending through a channel or passageway in said superstructure, conducting an occlusive surgical intervention at a second location in said target blood vessel on another side of said vascular pathology opposite said one side, the conducting of said occlusive surgical intervention including inserting a second flow occlusive medical device in a collapsed pre-deployment configuration through said channel or passageway via said catheter, the conducting of said occlusive surgical intervention further including expanding said second flow occlusive medical device from said collapsed pre-deployment configuration on a distal side of the expanded superstructure in said target blood vessel to form a first flow-occlusion implant;
after completion of said occlusive surgical intervention, removing said catheter from said channel or passageway;
permanently closing said channel or passageway after withdrawal or removal of said catheter from said superstructure; and
after the permanent closing of said channel or passageway, leaving said first flow occlusive medical device implanted in said target blood vessel to form a second flow-occlusion implant therein spaced from said first flow-occlusion implant.

17. The method defined in claim 16, further comprising, after the conducting of said occlusive surgical intervention, embolizing, with liquid embolics or sclerosants, collateral vessels or side branches of said target blood vessel between said second flow occlusive medical device and said superstructure, wherein said collateral vessels or side branches are related to varicoceles or varices.

18. A medical method comprising:
providing an occlusive medical device having a superstructure, at least one energized spring-loaded mechanical closure element being attached to said superstructure at a proximal end thereof;
inserting, into a target body cavity or conduit of a patient in an upstream direction counter to fluid flow through said target body cavity or conduit, said occlusive medical device with said superstructure in a collapsed configuration and with said at least one energized spring-loaded mechanical closure element in a channel-open pre-firing configuration disposed with said proximal end on a downstream side of said superstructure in said target body cavity or conduit;
thereafter expanding said superstructure from the collapsed configuration to a partially expanded deployment or use configuration inside said target body cavity or conduit so that a distal end portion of the partially expanded superstructure of said occlusive medical device extends across the target body cavity or conduit and engages an endothelial surface of the target body cavity or conduit;
via a catheter extending through a channel or passageway in said superstructure, conducting a surgical intervention on a distal side of the expanded superstructure in said target body cavity or conduit;
maintaining said distal end portion of said partially expanded superstructure in contact with the endothelial surface of the target body cavity or conduit-and holding a proximal end portion of said superstructure in a pre-expansion collapsed state spaced from and out of engagement with said endothelial surface during the conducting of said surgical intervention;
after a completion of said surgical intervention, removing said catheter from said channel or passageway; and
permanently closing said channel or passageway after the removing of said catheter from said channel or passageway, the permanent closing of said channel or passageway including automatically operating said at least one energized spring-loaded mechanical closure element to permanently close said channel or passageway independently of ambient fluid pressure in the target body cavity or conduit;
after the permanent closing of said channel or passageway by the operating of said at least one energized spring-loaded mechanical closure element, expanding said proximal end portion of said superstructure from said pre-expansion collapsed state so that said proximal end portion is in contact with said endothelial surface of the target body cavity or conduit; and
after the expanding of said proximal end portion, leaving said occlusive medical device implanted in said target body cavity or conduit to form a flow-occlusion implant therein.

19. The method defined in claim 18, wherein the permanent closing of said channel results in complete cessation of fluid flow through said channel or passageway.

20. The method defined in claim 18, wherein said at least one energized spring-loaded mechanical closure element is disposed to one side laterally of said channel or passageway, the operating of said at least one energized spring-loaded, mechanical closure element including curling said at least one energized spring-loaded mechanical closure element.

21. The method defined in claim 18, wherein said at least one energized spring-loaded mechanical closure element is one of a plurality of energized spring-loaded mechanical closure elements angularly equispaced at a trailing or proximal end of said occlusive medical device and extending proximally of said superstructure, said plurality of energized spring-loaded mechanical closure elements having a pre-closure configuration tapering down in a proximal direction away from said superstructure.

22. The method defined in claim 21 wherein said occlusive medical device has excess or unsupported membrane material that extends beyond terminal ends of said energized spring-loaded mechanical closure elements and that is crimpable or flattenable to form an ancillary closure secondary to constriction or folding over of the terminal material by said energized spring-loaded mechanical closure elements in a fully deployed state of said occlusive medical device.

23. The method defined in claim 18, wherein said catheter holds said at least one energized spring-loaded mechanical closure element in said channel-open pre-firing configuration during the conducting of said surgical intervention, the removing of said catheter from said channel or passageway enabling the automatic operating of said at least one energized spring-loaded mechanical closure element.

24. The method defined in claim 18, wherein said at least one energized spring-loaded mechanical closure element is disposed in a trailing tubular tail section that surrounds said catheter, said catheter traversing said trailing tubular tail section.

25. The method defined in claim 18, wherein said at least one energized spring-loaded mechanical closure element is incorporated into said superstructure.

26. The method defined in claim 18; wherein said catheter is a first catheter, the conducting of said surgical intervention including providing a second catheter coaxially inside said first catheter, extending said second catheter distally of a distal end of said first catheter, performing an intravascular operation via said second catheter, and removing said second catheter after said surgical intervention.

27. A medical method comprising:
providing a flow occlusive medical device having a superstructure;
inserting, into a vascular system of a patient, said medical device with said superstructure in a collapsed configuration;
thereafter expanding said superstructure from the collapsed configuration to a partially expanded deployment or use configuration inside a target blood vessel in the vascular system of the patient so that a distal end portion of the partially expanded superstructure of said flow occlusive medical device extends across the target blood vessel and engages an endothelial surface of such blood vessel in flow occluding contact and so that a proximal end portion of said superstructure remains in a pre-expansion collapsed state spaced from and out of engagement with said endothelial surface during the conducting of said surgical intervention;
via a catheter extending through a channel or passageway in said superstructure, conducting a surgical intervention on a distal side of the expanded superstructure in said target blood vessel;
maintaining said distal end portion of said partially expanded superstructure in flow occluding contact with the endothelial surface of the target blood vessel and holding said proximal end portion of said superstructure in said pre-expansion collapsed state spaced from and out of engagement with said endothelial surface during the conducting of said surgical intervention;
after completion of said surgical intervention, removing said catheter from said superstructure;
permanently closing said channel or passageway after withdrawal or removal of said catheter from said superstructure; and
after the permanent closing of said channel or passageway, expanding said proximal end portion of said superstructure from said pre-expansion collapsed state so that said proximal end portion is in contact with said endothelial surface of the target body cavity or conduit; and
after the expanding of said proximal end portion, leaving said flow occlusive medical device implanted in said target blood vessel to form a flow-occlusion implant therein spaced from a site of said surgical intervention.

28. The method defined in claim 27 wherein the conducting of said surgical intervention includes inserting a flow-occlusion implant in said target blood vessel.

29. The method defined in claim 27, wherein said catheter is a first catheter, the conducting of said surgical intervention including providing a second catheter coaxially inside said first catheter, extending said second catheter distally of a distal end of said first catheter, performing an intravascular operation via said second catheter, and removing said second catheter after said surgical intervention.

30. The method defined in claim 27, further comprising adjusting a position of said first occlusive device after performance of said surgical intervention and prior to expanding said proximal end portion of said superstructure from said pre-expansion collapsed state.

31. A medical method comprising:
providing a flow occlusive medical device having a superstructure;
inserting, into a target blood vessel of a patient in a direction counter to blood flow, said medical device with said superstructure in a collapsed configuration;
thereafter expanding said superstructure of said flow occlusive medical device from the collapsed configuration to an at least partially expanded deployment or use configuration inside the target blood vessel so that the at least partially expanded superstructure extends across the target blood vessel and engages an endothelial surface of such blood vessel downstream of a vascular pathology to cause flow cessation or arrest through said target blood vessel;
via a catheter extending through a channel or passageway in said superstructure, conducting an occlusive surgical intervention to insert or deploy a first flow-occlusion implant on a distal side of the at least partially expanded deployment or use configuration of said superstructure and on a upstream side of said vascular pathology;
after completion of said occlusive surgical intervention, removing said catheter from said superstructure;
permanently closing said channel or passageway after withdrawal or removal of said catheter from said superstructure; and
after the permanent closing of said channel or passageway, leaving said flow occlusive medical device implanted in said target blood vessel to form a second flow-occlusion implant therein spaced from said first flow-occlusion implant and to create therewith a segmental vessel occlusion of said vascular pathology.

* * * * *